US006846654B1

(12) United States Patent
Blackburn et al.

(10) Patent No.: US 6,846,654 B1
(45) Date of Patent: Jan. 25, 2005

(54) CATALYTIC ANTIBODIES AS CHEMICAL SENSORS

(75) Inventors: Gary F. Blackburn, Gaithersburg, MD (US); Charles Durfor, Rockville, MD (US); Michael J. Powell, Gaithersburg, MD (US); Richard J. Massey, Rockville, MD (US)

(73) Assignee: IGEN International, Inc., Gaithersburg, MD (US)

( * ) Notice: Subject to any disclaimer, the term of this patent is extended or adjusted under 35 U.S.C. 154(b) by 1174 days.

(21) Appl. No.: 08/090,245

(22) Filed: Jul. 9, 1993

Related U.S. Application Data

(63) Continuation-in-part of application No. 06/566,016, filed on Nov. 29, 1983, now abandoned, which is a continuation of application No. 07/657,623, filed on Feb. 20, 1991, now abandoned, which is a continuation of application No. 07/138,542, filed on Dec. 24, 1987, now abandoned, which is a continuation-in-part of application No. 06/674,253, filed on Nov. 27, 1984, now Pat. No. 4,888,281, which is a continuation-in-part of application No. 07/830,991, filed on Feb. 5, 1992, now abandoned.

(51) Int. Cl.$^7$ .......................... G01N 33/53; C07K 16/00
(52) U.S. Cl. ........................... 435/71; 435/76; 435/772; 435/188.5; 435/817; 530/388.1; 530/391.1
(58) Field of Search ................................ 435/188.5, 7.1, 435/7.6, 7.72, 817; 530/388.1, 391.1

(56) References Cited

U.S. PATENT DOCUMENTS

| | | | | |
|---|---|---|---|---|
| 4,050,895 A | * | 9/1977 | Hardy ..................... | 436/805 X |
| 4,151,252 A | * | 4/1979 | Marchand ................ | 422/51 |
| 4,196,265 A | | 4/1980 | Koprowski et al. | |
| 4,238,757 A | * | 12/1980 | Schenck ................... | 436/806 X |
| 4,314,821 A | * | 2/1982 | Rice ........................ | 436/806 X |
| 4,376,110 A | | 3/1983 | David et al. | |
| 4,525,265 A | * | 6/1985 | Abe ......................... | 435/817 X |
| 4,579,642 A | * | 4/1986 | Niiyama ................. | 435/817 X |
| 4,637,861 A | * | 1/1987 | Krull ....................... | 435/817 X |
| 4,659,567 A | * | 4/1987 | Tramontano et al. ..... | 435/188.5 |
| 4,713,165 A | * | 12/1987 | Conover et al. ........... | 204/403 |
| 4,792,446 A | * | 12/1988 | Kim et al. ............... | 435/188.5 |
| 4,822,566 A | * | 4/1989 | Newman ................... | 422/68 |
| 4,888,281 A | * | 12/1989 | Schochetman et al. .. | 435/188.5 |

OTHER PUBLICATIONS

Kohen et al., "Antibody–Enhanced Hydrolysis of Steroid Esters," Biochim Biophys Acta 629: 328–337(1980).*
Kohen et al., "Monoclonal Immunoglobulin G Augments Hydrolysis . . . ," FEBS Lett 111:427–431 (1980).*
Kohen et al., "A Steroid Immunoassay Based on Antibody–Enhanced . . . ," FEBS Lett 100:137–140 (1979).*
L.Slobin, "Prep. and Some Properties Of Antibodies With Specificity Towards p–Nitrophenylesters", Biochemistry, 5 2836–2844 (1966).
W. Raso and B.D. Stollar, The Antibody Enzyme Analogy, Characterization of Antibodies To Phosphopyriodoxyltyrosine Derivatives. Biochemistry, 14, 584–591 (1975).
V. Raso and B.D. Stollar, "The Antibody Enzyme Analogy. Compr. of Enzymes and Antibodies Specific For Phosphopyriodoxyltyrosine.", Biochemistry, 14, 591–599 (1975).
J. Burd et al., "Specific Protein–Binding Reactions Monitored By Enzymatic Hydrolysis Of Ligands–Fluorescent Dye Conjugates", Analytical Biochemistry, 77, 56–67 (1977).
F. Kohen et al., "A Steroid Immunoassay Based On Antibody–Enhanced Hydrolysis Of A Steroid–Umbelliferone Conjugate", FEBS Letters, 100, 137–140 (1979).
F. Kohen et al., "Nonradioisotopic Homogeneous Steroid Immunoassays", J. Steroid–Biochemistry, 11, 161–167 (1979).
Erhan, S. and Greller, L. D., Nature, vol. 251 353 (1974).
F. Cohen et al., "Antibody–Enhanced Hydrolysis Of Steroid Esters", Biochimica et Biophysica Acta, 629, 328–337 (1980).
F. Kohen et al., "Monoclonal Immunoglobulin G Augments Hydrolysis of An Ester Of The Homologous Hapten", FBS Letters, 111, 427, 431 (1980).
S.J. Pollack, "Selective Chemical Catalysis By An Antibody", Science, 234, 1570–1573 (1986).
A. Tramontano, "Catalytic Antibodies,", Science, 234, 1566–1570 (1986).
K. Moe, "Scripps, UC Create 'Killer' Antibodies", S.D. Union, Dec. 12, 1986.
"Making Antibodies Act Like Enzymes", Science News, 130, Nos. 25 & 26, Dec. 20 & 27, 1986.
Bulletin, Office Of Public Information, Berkeley Campus, University of California, Dec. 9, 1986.

* cited by examiner

Primary Examiner—Michael P. Woodward
(74) Attorney, Agent, or Firm—Kramer Levin Naftalis & Frankel LLP; Barry Evans, Esq.

(57) ABSTRACT

A system for detecting physical or chemical changes in an environment is disclosed. The system comprises means for conducting a chemical reaction; an active biological molecule whose physiological function is noncatalytic which is capable of catalyzing a chemical reaction wherein at least one reactant is converted to one product; and means for sensing and processing information relating to changes in said environment. A method for detecting physical or chemical changes in an environment is also disclosed.

3 Claims, 19 Drawing Sheets

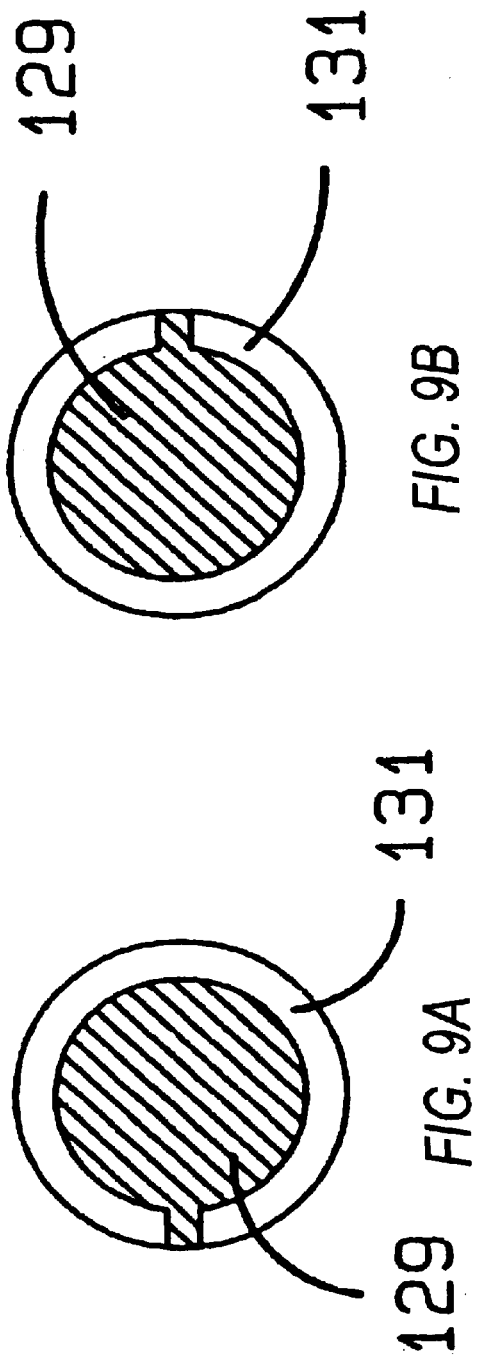
FIG. 9A
FIG. 9B
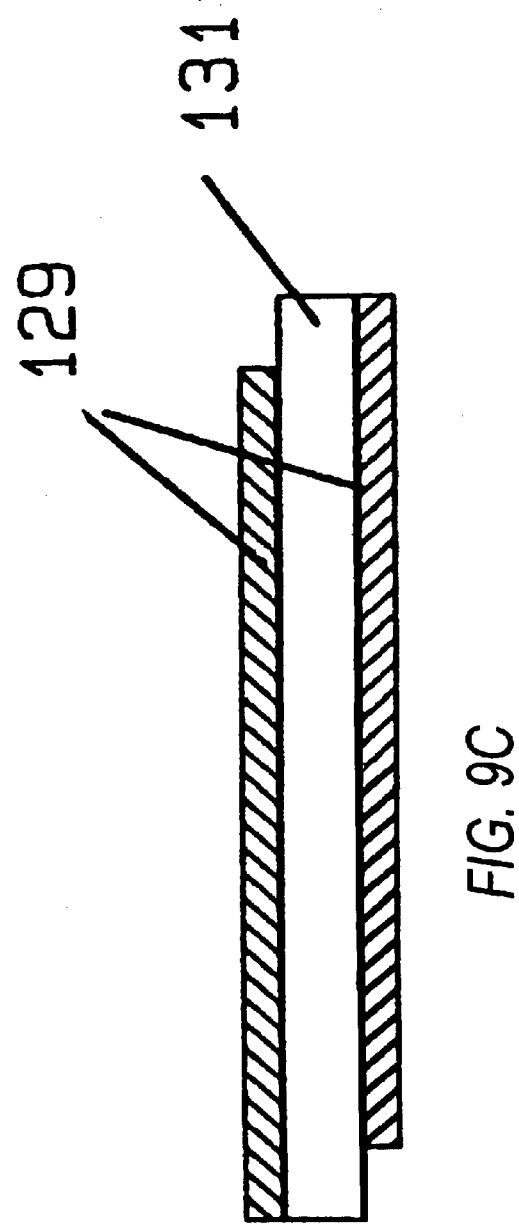
FIG. 9C

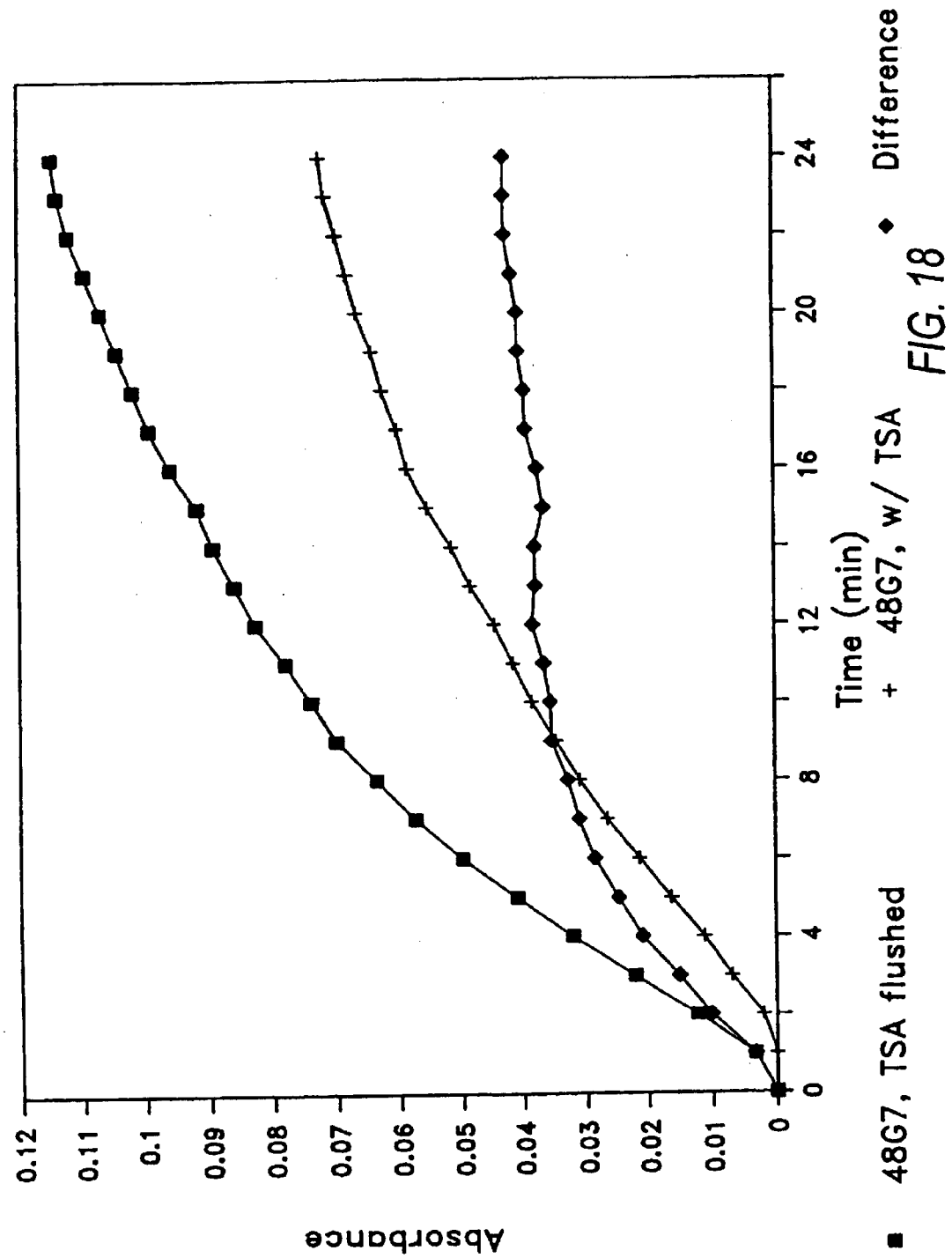

CATALYTIC ANTIBODIES AS CHEMICAL SENSORS

This application is a continuation of application Ser. No. 07/138,542, filed Dec. 24, 1987, now abandoned which application is a continuation-in-part of application Ser. No. 06/674,253, filed Nov. 27, 1984, now U.S. Pat. No. 4,888, 281, which in turn is a continuation of application Ser. No. 07/657,623, filed Feb. 20, 1991, now Abn. which is a continuation of application Ser. No. 07/138,542, filed Dec. 24, 1987, now abandoned, which in turn is a continuation of application Ser. No. 07/830,991, filed Feb. 5, 1992, Abn. which in turn is a continuation-in-part of appln. Ser. No. 06/566,016 filed Nov. 29, 1983, now Abn.

FIELD OF THE INVENTION

This invention pertains generally to chemical sensors and more particularly to chemical sensors which incorporate catalytic antibodies capable of reversibly binding to an antigen and/or catalyzing the reaction of one or more reactants to one or more products.

This application is a continuation-in-part of U.S. application Ser. No. 674,253, filed Nov. 27, 1984, which is a continuation-in-part of U.S. application Ser. No. 556,016, filed Nov. 29, 1983, now abandoned, the contents of which applications are hereby incorporated by reference into this application.

Several publications are referenced in this application by Arabic numerals within parentheses. Full citations for these references are found at the end of the specification immediately preceding the claims. The disclosures of these publications are incorporated by reference into this application in order to more fully describe the state of the art to which this invention pertains as well as to more fully describe the invention itself.

BACKGROUND OF THE INVENTION

The development of chemical sensors began in 1906 when it was discovered that the electrochemical potential at certain thin glass membranes depended upon the hydrogen ion concentration in the bathing solution (1). As a result of this discovery, the first pH electrode was reported in 1909 (2). Since that time, development of chemical sensors has been considerable with blood gas and electrolyte measurement systems having undergone substantial development. In comparison, development of sensors for the detection of metabolites and biomolecules has not progressed as far.

The term "biosensor" usually denotes a sensor which is specific for biological substances. However, the term is often used to specify a sensor which uses biological substances to detect other chemicals. A biosensor is a monitoring device whose selectivity in detecting an analyte is the result of the binding specificity of a biological molecule, e.g., antibody, enzyme or membrane receptor. Analyte concentrations are determined by "transducing" these analyte binding events into a measurable quantity such as an electronic or optical signal. Thus, the basic components of a biosensor are a biological molecule, e.g., antibody, enzyme or membrane receptor, and a transducer.

Biosensors generally fall into three basic categories: electrochemical; optical; or physical. These biosensors incorporate transducers which are well known to the skilled artisan and include calorimetric, piezoelectric, amperometric, optical fiber, optical waveguide, lipid membrane, potentiometric and electrochemical capacitance/impedance devices.

While the aforementioned biosensor transduction techniques and devices may be employed in the invention, future improvements in miniaturization and in other analytical techniques such as mass spectroscopy, gas chromatography and nuclear magnetic resonance spectroscopy may allow such other techniques and systems to also be used in the invention.

The biological component of preexisting biosensors is either an enzyme, an antibody, a membrane receptor, whole cell or tissue. Enzymes, antibodies and membrane receptors are all biological macromolecules whose function is to bind target molecules in a highly specific manner. While integration of enzymes and receptors into sensors appeared to have great potential, their commercial application is often limited.

Sensors incorporating enzymes can detect many chemicals. However, the chemicals which can be detected are limited to those for which stable enzymes are available and still further to those enzymes which either consume or produce measurable molecules. Yet a large number of chemicals are consumed or produced by chemical reactions for which there are no known enzyme catalysts. Biosensors which rely upon enzymes are also limited to the extent that the enzymes are limited in their function by allosterism. Allosteric enzymes are enzymes which are stimulated or inhibited by a modulator molecule which may be the substrate, the product or some other molecule. As a result of allosterism, the kinetic behavior of such enzymes is greatly altered by variations in the concentration of the modulator. A relatively simple example of allosteric behavior is where the enzyme is subject to feedback inhibition, i.e., where the catalytic efficiency of the enzyme decreases as the concentration of an intermediate or subsequent product increases. Use of such enzymes in many biosensor applications is thus limited and requires continuous removal of product.

A further major disadvantage of enzyme sensors is attributable to the fact that the binding affinity of the analyte is determined by its biological role. Most enzymes possess binding affinities in the $10^3$–$10^6 M^{-1}$ range and the binding affinity determines the sensitivity of the enzyme sensor. Thus most enzyme sensors have, at best, nanomolar detection limits.

As to membrane receptors, there is difficulty in isolating sufficient quantities of protein. Moreover, the commercial application of membrane receptors in sensors is often limited by their inherent instability and by the need for highly ordered and easily degraded environments.

Sensors incorporating antibodies as the biological component, like enzymes, have high selectivity but can have substantially improved detection limits as compared to enzymes due to the higher binding affinities of antibodies. Antibodies have binding affinities of $10^5$–$10^{13} M^{-1}$ and thus sensors incorporating antibodies can have detection limits in the picomolar range. Antibodies are limited, however, by the fact that the recognition and identification of antigens by antibodies via immunological reactions is usually a one-time event. As antigen saturates antibody, the development of a specific antigen-antibody complex can be measured. However, whether monoclonal or polyclonal antibodies are used for antigen capture, this reaction (with high affinity bindings and hence improved detection limits) is usually not readily reversible. The antibody-based sensor thus becomes saturated and the presence of analytes in a subsequent sample cannot be detected. The inability to repeatedly use such sensors is a major limitation.

A common method for dissociating antigen-antibody complexes involves incubating the antibody in either low pH solutions or high concentrations of salt, urea or thiocyanate. While such methods can regenerate an antigen binding site, each procedure requires careful control of the reaction conditions and may cause partial protein denaturation, especially after several regeneration cycles. The absence of a reliable method for regenerating an antigen binding site immediately after each binding event has frustrated the development of a sensing system capable of monitoring successive exposures to a given analyte.

It can be readily appreciated that a durable sensing system with high sensitivity which is capable of repeatedly detecting and measuring the concentration of an analyte over large concentration ranges and which is capable of being calibrated without antigen saturation would be a highly desirable advance over the current state of the art in sensing systems.

OBJECTS, FEATURES AND ADVANTAGES OF THE INVENTION

It is therefore a general object of the invention to provide a sensing system which incorporates an antibody capable of reversibly binding with an antigen.

It is a further object of the invention to provide a highly sensitive sensing system capable of detecting extremely low concentrations of analyte.

It is another object of this invention to provide a highly sensitive sensing system capable of detecting analyte over large concentration ranges.

It is another object of the invention to provide a reversible sensing system having the ability to measure both increases and decreases of the concentration of an analyte without the need for a separate regeneration process between samples.

It is another object of the invention to provide a sensing system which incorporates an antibody which permits the system to be calibrated without antigen-combining site saturation.

It is yet another object of the invention to provide a sensing system having the ability to employ new catalytic binding sites for novel analytes.

It is another object of the invention to provide a sensing system with catalytic combining sites having properties similar to membrane receptors.

It is yet another object of the invention to provide a sensing system capable of detecting substances consumed or generated by reactions for which there are no known enzyme catalysts.

It is another object of the invention to provide a sensing system which can detect physical or chemical changes in an environment as the result of the consumption or generation of an analyte by a chemical reaction.

It is another object of the invention to provide a sensing system which incorporates a catalytic antibody which can reversibly bind to an antigen.

It is yet another object of the invention to provide a sensing system which incorporates a catalytic monoclonal antibody which can reversibly bind to an antigen.

It is yet another object of the invention to provide a sensing system containing an antibody wherein the antigen binding site is regenerable immediately after each binding event.

It is another object of the invention to provide a sensing system containing an antibody for detection of an analyte which inhibits the catalytic effectiveness of the antibody.

These and other objects, features and advantages of the invention are achieved by the invention.

SUMMARY OF THE INVENTION

The invention is broadly directed to a system for detecting physical or chemical changes in an environment. The system comprises means for conducting a chemical reaction, an active biological molecule whose physiological function is noncatalytic which is capable of catalyzing a chemical reaction in the environment, a transducer capable of detecting physical or chemical changes in the environment caused by the binding of the antibody or the subsequent chemical reaction and further capable of generating information relating to those changes and means for processing the information generated by the transducer in response to those changes. Desirably, the active biological molecule is one which has been rationally transformed into, synthesized, or identified as a catalyst.

The invention is also directed to a method for detecting physical or chemical changes in an environment wherein the changes are the result of a chemical reaction (or a plurality of reactions) taking place in the environment in which at least one reactant is converted to at least one product. The method comprises the steps of causing the chemical reaction to take place in the environment by contacting the reactant with an active biological molecule under conditions which are conducive to the conversion of the reactant to the product, sensing physical or chemical changes taking place in the environment as a result of the chemical reaction and transducing those changes into information related thereto and processing the information generated by the transducer in response to the physical or chemical changes.

In another aspect, the invention is directed to a system for detecting the presence of an analyte of interest in an environment wherein the analyte of interest or some other component of the environment is consumed or generated during the course of the chemical reaction, i.e., a component which is a coreactant, coproduct, intermediate, precursor or other species which is formed or consumed due to one or more reactions in the environment. The system comprises means for conducting a reaction, an active biological molecule which is capable of catalyzing the chemical reaction, a transducer capable of detecting the presence or absence of a component of the environment, typically but not necessarily, a reactant or coreactant or a product or coproduct, and further capable of generating information relating thereto and means for processing the information generating by the transducer. Desirably the active biological molecule is one which has been rationally transformed into, synthesized, or identified as a catalyst.

The invention is also directed to a method for detecting an analyte of interest in an environment wherein the analyte or another component of the environment is consumed or generated during the course of the chemical reaction. The method comprises the steps of causing the chemical reaction to take place in the environment by contacting a reactant of the chemical reaction with an active biological molecule under conditions which are conducive to the conversion of the reactant to a product, sensing the presence or absence of a component of the environment as defined above, generating information relative thereto and processing the information generated by the transducer to determine the presence of the analyte of interest.

In another specific embodiment, the invention is directed to a system for detecting an analyte of interest in an environment wherein the analyte of interest or another component of the environment is consumed or generated during the course of a chemical reaction and wherein the transducer is capable of detecting binding of the analyte to the antibody and further capable of generating information related to that binding. The system comprises means for conducting a reaction, an active biological molecule which has been rationally transformed into, synthesized, or identified as being catalytic for the reaction and which is capable of binding a component of the environment, a transducer capable of detecting binding of the analyte to the antibody and generating information relative thereto and means to process that information to determine the presence of the analyte of interest.

In another embodiment the invention is a method for detecting an analyte of interest or other component in an environment which comprises causing the component to bind to a catalytic antibody, detecting the binding of the component to the antibody, transducing the data obtained from the binding event and generating information relating to that binding event, processing the information generated by the transducer and releasing the bound component from the antibody by allowing the antibody to catalyze a chemical reaction involving the bound component. The analyte or related component of the environment may be released from the antibody in the same environment or the complex may be removed to a separate environment where the analyte or related component is released.

Still other embodiments of the invention include systems and methods as described above for detecting the presence of chemicals which act as inhibitors of a chemical reaction catalyzed by an antibody. In such systems and methods the physical or chemical change in the environment or the presence or absence of a component of the environment is caused by inhibition of the antibody-catalyzed reaction.

BRIEF DESCRIPTION OF THE DRAWINGS

The invention, as well as other objects, features and advantages thereof will be understood more clearly and fully from the following description of certain preferred embodiments, when read with reference to the accompanying drawings, in which:

FIG. 9A shows a top view, FIG. 9B shows a bottom view and FIG. 9C shows a side view of crystals used as a bulk acoustic wave (BAW) chemical sensor; view (B) of crystals used as a bulk acoustic wave (BAW) chemical sensor;

FIG. 18 graphically depicts the sequential response to additions of 250 $\mu$M MpNPC; the plus symbols represent the response in the presence of TSA inhibitor; the square symbols represent the response after flushing away of the TSA inhibitor; and the diamond symbols represent the differential signal.

DETAILED DESCRIPTION OF THE INVENTION

Figure 1:
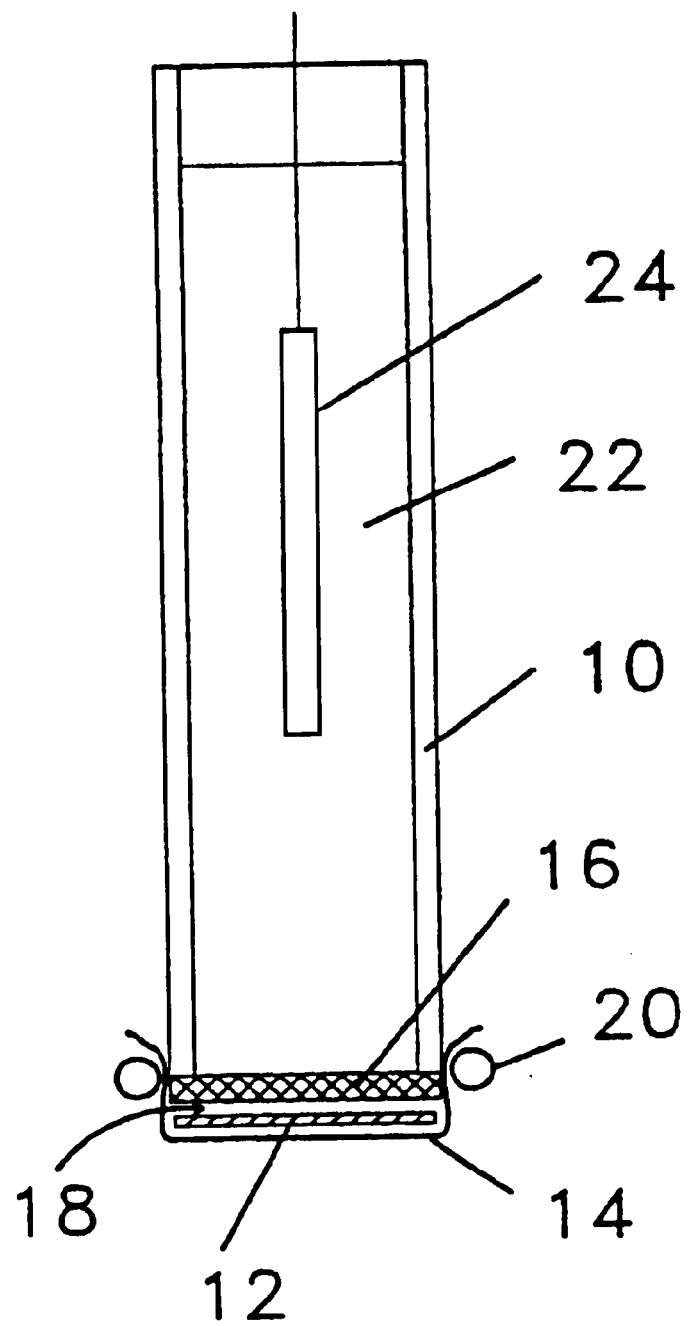
FIG. 1 is a schematic diagram of a pH-based catalytic antibody potentiometric biosensors.

Broadly, the invention relates to systems and methods for detecting physical or chemical changes in an environment or for detecting the presence of analytes of interest is an environment wherein an active biological molecule is employed to cause a environment reaction to take place, changes in the environment are sensed and the sensory data are transduced into information which can be processed to provide the measurements sought. By active biological molecule is meant, broadly, all biological molecules or aggregations thereof whose physiological function is non-catalytic. These are desirably species which have been rationally transformed into, synthesized, or identified as catalytic. The active biological molecules may be contained in or on cells, components of cells or tissue, and may be in purified or unpurified form.

The active biological molecules include, but are not limited to, catalytic antibodies, naturally occurring and synthesized species thereof, fragments of such antibodies, synthetic peptides derived therefrom and antibodies which have been rendered catalytic by chemical, physical or genetic modification, e.g., single chain antibodies. Rationally synthesized monoclonal antibodies are most highly preferred.

As used in the following detailed description of the invention, the term "detection" includes the concepts of measurement and quantitation. Such measurement and quantitation can be with respect to the total quantity of analytes of interest and/or the concentration thereof, and such measurements can be one-event, intermittent, or continuous as is known in the art.

The terms "reaction" and "means for conducting reaction" are used in their broadest sense. Reactions include, without limitation, oxidations, reductions, additions, transformations, condensations, eliminations, substitutions, cleavages, rearrangements, and other phenomena where a chemical species is consumed or transformed. By "consumed" is meant any phenomenon where the original species is changed, modified, or otherwise converted to a different chemical or physical species including an isomer. By "means for conducting a reaction" is broadly meant any vessel for containing an environment wherein an analysis is to be carried out, including containers, vessels, tanks, analysis equipment, probes, samples, conduits, and any other known means as are available or may become available in the art.

As used herein, the term "active biological molecule" means a biological molecule whose physiological function is noncatalytic. As will be apparent from the following discussion, such active biological molecules are preferably those which have been rationally transformed into, synthesized, or identified as catalytic for a given chemical reaction. Methods for such synthesis are described in application Ser. No. 674,253, filed on Nov. 27, 1984, and application Ser. No. 556,016, filed Nov. 29, 1983, the priority of which applications is claimed. A further description of the methods for rationally transforming, synthesizing, or identifying active biological molecules, particularly monoclonal antibodies, are known in the literature.

A "biological molecule" is broadly defined as a molecule which has been constructed from the compounds from which organisms are formed. Such compounds can be amino acids, nucleic acids, saccharides, membrane lipids, or biological cofactors.

Amino acids include the twenty essential amino acids and other amino acids which can be incorporated into proteins. Molecules constructed from amino acids also include peptides, i.e., chains composed of amino acids linked together through peptide bonds. These can be molecules such as neurotransmitters, hormones, and/or peptides derived from the functional parts of larger peptides. Molecules construced from amino acids also include proteins, i.e., longer chained peptides which may have one of many noncatalytic functions such as electron transfer proteins (e.g., ferredoxins and flavodoxins), immune protection proteins (antibodies), proteins that generate or transmit nerve impulses (e.g., acetylcholine, dopamine, and the rhodopsin membrane receptors), structural proteins (e.g., collagen, fibrin, glycoproteins, elastin, etc.), other binding proteins (e.g., histones), and mass transport proteins (e.g., ferritin, hemoglobin).

Saccharides include monosaccharides (e.g., glucose, fructose, etc.), oligosaccharides (e.g., sucrose, raffinose, etc.), and polysaccharides (e.g., starch—a fuel storage molecule; and cellulose—a structural molecule). Membrane lipids include molecules such as phospholipids (e.g., lipid bilayer membranes and other fatty acids), glycolipids, cholesterol and its derivatives, and prostaglandin and its derivatives. Nucleic acids include the five common nucleotides (adenine, guanine, cytosine, uracil, and thymine), oligonucleotides, and polynucleotides or nucleic acids such as DNA, m-RNA, and t-RNA. Cofactors are biological molecules whose catalytic function may not be generated or specifically directed until associated with a polypeptide chain. Examples are riboflavin derivatives, porphyrins, thiamin pyrophosphate and nicotinamide adenine dinucleotide, etc.

As used herein, the term "antigen" means any molecule which is specifically bound by an active biological molecule as defined above and further in the specific description of the invention.

The preferred active biological molecules used in the sensors of the invention are catalytically active antibodies, fragments thereof, or synthetic peptides derived therefrom. Still further preferred are monoclonal antibodies which have been synthesized as catalysts according to the methods taught in the priority applications and further described below.

The active biological molecules may be used in the sensors of the invention per se or may be contained in or on cells or cellular components or on tissue, and they may be in purified or unpurified form.

The detection systems of the invention generally include an active biological molecule, typically referred to hereinafter as an antibody capable of catalyzing a chemical reaction (a "catalytic antibody"), a transducer capable of detecting events taking place as a result of the chemical reaction and further capable of generating information relating to those events and means for measuring the information so generated. In general, the events which are detected by the transducer may be the appearance or disappearance of chemical species including, inter alia, reactants, coreactants, products, coproducts, precursors, intermediates or such species as may be involved in follow-on reactions or may be physical or chemical changes in the environment due to the reaction or binding of the catalytic antibody and one or more of such species. The transducer detects these events by sensing any number of changes in physical or chemical phenomena including but not limited to changes in pH, temperature, ionic state, impedance/capacitance properties, mass, emission characteristics (e.g., fluorescence and electrogenerated chemiluminescence), absorption characteristics and reflection characteristics of light of various wavelengths, changes in electrical potential, wave propagation, substrate binding, etc. These events are associated with a chemical reaction or reactions taking place in the environment.

The invention also is in a method for detecting various events taking place in an environment. These methods employ the detection systems of the invention and generally comprise either causing a chemical reaction to take place in an environment by contacting a reactant with an active biological molecule, e.g., a catalytic antibody or causing a catalytic antibody to bind to a component of the environment and then using the detection systems of the invention to detect and/or quantify the events taking place in the environment as a result of the chemical reaction or the antibody binding.

Catalytic antibodies are usually produced by immunizing animals with molecules which are designed to mimic the structure and charge distribution of the transition state for the reaction to be catalyzed. The animals make many different antibodies for the transition state analog (TSA) having different amino acid sequences and, consequently, different binding affinities and catalytic activities. Careful screening of the various antibodies for binding and catalytic activity yields antibodies which catalyze the reaction of interest.

It will be understood that the binding of a catalytic antibody to its reactant (antigen) is different than the binding of a noncatalytic antibody to its antigen. While both kinds of antibodies bind by ionic and Van der Waals forces and by hydrophobic partition forces, the binding of a normal high affinity ($10^9$–$10^{14}M^{-1}$) antibody to an antigen is very slow to reverse under the binding conditions and is practically irreversible.

In contrast to noncatalytic antibodies, catalytic antibodies bind reversibly to an antigen. Catalytic antibodies catalyze chemical reactions in which the reaction products are not permanently bound by the antibody and the free antibody combining site is regenerated as the product is formed and diffuses away from the antibody. The catalytic antibody thus is regenerated without altering the environmental conditions and is ready for another cycle of catalysis. Further, because catalytic antibodies bind reversibly, the sensors of the invention respond reproducibly and continuously to decreasing as well as increasing concentrations of analyte.

The reversible binding ability of catalytic antibodies is especially significant in view of the fact that recognition and identification of antigens by antibodies is a one-time event. Typically, as antigens saturate the antibody, the development of a specific antigen-antibody complex can be measured. However, whether monoclonal or polyclonal antibodies are used for antigen capture, this reaction is usually not readily reversible. As a result, the presence of specific analytes in the same or in a subsequent sample cannot be detected. Their inability to repeatedly recognize analytes is a major limitation in using noncatalytic antibodies as components of sensing systems.

The recent identification of antibodies having catalytic activity offers new methods of regenerating antigen binding sites. Integration of catalytic antibodies into sensor systems not only avoids the usual problems of dissociating an antigen-antibody complex, creating a reversible sensor, but also permits a sensor to detect analyte concentrations over large concentration ranges and to be calibrated without antibody site saturation. In addition, the ability to form new catalytic antibodies and hence new catalytic sites for novel analytes or to form catalytic sites with binding properties similar to membrane receptors opens important new areas for development of catalytic antibody sensors. Since a catalytic antibody can potentially be engineered for any analyte, a sensor incorporating a catalytic antibody specific for a certain analyte can detect that analyte under circumstances where it might otherwise be undetectable.

Sensors according to the invention have applications in several different areas. An important area is that of clinical medicine, where many different analytical instruments and techniques are currently employed to determine the concentration of clinically important chemicals. Until recently, radioimmunoassay techniques were used for most chemical analyses but these require typically large and expensive instruments designed for large centralized hospital or clinical laboratories. Pressure to cut health care costs is now creating more demand for less expensive, smaller analyzers which can be used in decentralized organizations, e.g., in individual hospital wards, outpatient departments, and physicians' offices. The biosensors of the invention, as a result of their small size, low cost, selectivity, and sensitivity, may well serve that need. Reliable chemical sensors already exist for potassium, sodium, hydrogen, lithium, and calcium ions but have yet to be developed for most proteins, hormones, metabolites, and organic drugs.

Veterinary health care is another area having needs similar to those of the human health care field. Biosensors may have many potential applications in the diagnosis and monitoring of animal health problems.

Another potentially large area of use for biosensors is that of fermentation control (3). There are many industrial applications of biochemical and microbiological processes in fields such as the production of food, pharmaceuticals, wastewater treatment and energy production. Fermentation reactions also have an important role in such biotechnological processes. It is necessary to carefully control the systems involved to optimize production. Rapid and sensitive on-line monitoring and control of reactant and product concentrations, reaction conditions and the like call for sensors specific to the substrates and products of fermentation.

Environmental monitoring is another growing area wherein biosensors are needed (4). Rising concerns over atmospheric, water, and soil pollution are creating a demand for chemical sensors to monitor substances such as pesticides, phenols, phenoxyacids, nitrilotriacetate, heavy metals, nitrate, phosphate, sulphate, and urea.

The defense industry also has a need for sensitive chemical sensors to monitor trace levels of chemical and biological warfare agents. Other applications for chemical sensors include food and feed process and quality control, agricultural diagnostics and monitoring, industrial hygiene, and toxicology testing.

Catalytic Antibodies

Antibodies capable of catalyzing a chemical reaction are defined as "catalytic antibodies." Catalytic antibodies are identified and described in Schochetman and Massey, application Ser. No. 674,253 filed Nov. 27, 1984, referred to above in the "Statement of the Invention."

During the course of a chemical reaction, the reactants undergo one or more transitions through structures which are energetically less favorable than either the reactant or product. In molecular terms, these transition states (or intermediate structures) reflect changes in bond lengths and bond angles as well as bond formations and breakages. The energy required to achieve a transition state is denoted as the activation energy, which may also be considered as the difference in energy between the energy of the transition state and the energy of the reactants.

Catalysts increase chemical reaction rates by lowering the activation energy of a reaction. Antibodies elicited to a hapten or antigen, which immunogens are chosen because, inter alia, they resemble the presumed transition state structure (i.e., a transition state analog) can catalyze reactions. The antibody thus produced should stabilize the energy of the transition state relative to reactants and products. This approach has been successfully demonstrated in the generation of several catalytic monoclonal antibodies.

Thus, the specific application of this approach requires immunization of mice with a transition state analog, reactant, or product compound, or these compounds after covalently bonding them to a carrier protein such as bovine serum albumin or keyhole limpet hemocyanin. Once an immune response is detected in the mouse serum, polyclonal antibodies can be isolated from that serum by a combination of ammonium sulfate fractionation, molecular radius and affinity chromatographic techniques. Because this preparation of antibodies is polyclonal, a variety of proteins will be present which bind the transition state structure with differing specificity, avidity, and isotype. The distribution of antibody molecules will change as the animal's immune response matures.

In contrast, a monoclonal antibody cell line produces a single antibody which binds to the transition state analog structure at a defined idiotope and with a defined affinity. These cell lines are produced by fusing a specific B cell (isolated from the mouse which demonstrated an immune response) with an appropriate myeloma tumor cell. This cell line can be maintained by tissue culture or in vivo passage of the tumor in mice.

Thus, catalytic antibodies may be either monoclonal or polyclonal antibodies. The advantage of monoclonal catalytic antibodies is the ability to screen a large number of cell lines and specifically identify an antibody which not only binds tightly to the eliciting transition state analog, but also displays maximal catalytic activity. In addition, hybridoma cell lines provide a constant, inexpensive source of chemically identical antibodies. Methods for producing monoclonal antibodies are well known in the art. (Koprowski, H. et al., U.S. Pat. No. 4,196,265, issued Apr. 1, 1980.)

Major limitations are associated with traditional chemical and enzymatic catalysts for both synthesis and sensor applications. Chemically catalyzed processes often require high temperatures and pressures and may not produce high yields of the desired product. This is because harsh reaction conditions and the lack of reaction specificity often result in the formation of undesirable side reactions. Furthermore, chemical catalysts are unknown for many important reactions and the rational design of future catalysts is extremely difficult. Other limitations existing with commercial chemical catalysts are their relatively high cost, a requirement for chemical activation, their inability to function at atmospheric pressure and/or in the presence of trace quantities of water, and potential problems with flammability or explosion in the presence of atmospheric oxygen.

While both enzymes and antibody catalysts can be used effectively in aqueous solutions at room temperature, industrial applications of enzymatic catalysts in synthesis and sensors are limited by the requirement that naturally occurring enzymes with the desired reaction specificity be identified. Thus, many enzymes which catalyze industrially important reactions have yet to be isolated. Other limitations of enzymatic catalysis are protein instability, difficulty in isolation, the requirement for exotic reactants (e.g., redox or transaminase compounds), as well as allosteric inhibition of enzymatic catalysis (which is a fundamental part of an enzyme's physiological function).

In contrast, rationally designed monoclonal antibodies are ideal for many synthetic and sensor applications. Large scale production of these proteins is well defined, detection specificity can be as broad or as specific as the eliciting hapten, immunoglobins are extremely stable biomolecules with respect to temperature and time, allosteric inhibition is not a problem, and both substrate binding affinities and turnover numbers can be selected from a family of catalytic monoclonal antibodies elicited by a single transition state analog. In addition, because an antibody catalyst can be designed to accelerate a reaction by a different pathway than an existing enzyme, requirements for expensive coreactants may be alleviated. The advantage can also be of particular value in defining new reaction conditions (e.g., pH requirements), or in identifying mechanisms for controlling the rate of antibody binding site regeneration (e.g., esterase antibody catalysts demonstrate a first order dependence on hydroxide ion, esterase enzymes do not). While all of these examples demonstrate the significant advantages of using antibody catalysts in either synthetic or sensor applications, the most important advantage is that a catalyst can be designed for almost any analyte.

Catalytic antibodies may also be used to increase the rate or site and stereospecificity of reactions catalyzed by non-proteinaceous molecules such as biological cofactors and coenzymes or nonbiologically derived cofactors. Examples of the former class of compounds include, but are not limited to, porphyrins, flavins, nicotinamide adenine dinucleotide, pyridoxal phosphate, biotin, or tetrahydrofolate derivatives. Examples of nonbiologically based cofactors include, but are not limited to, aluminum porphyrins, 4-ethylpyridine , and platinum or palladium catalysts.

Catalytic antibodies described heretofore are useful in accelerating the reaction rates for a variety of chemical transformations. These reactions may be unimolecular, bimolecular, or even more complex in nature. They may catalyze reactions similar to those catalyzed by enzymes such as oxidations, reductions, isomerizations, additions or eliminations from double bonds, condensations, substitutions, hydrolyses, or rearrangements. They may also catalyze nonbiologically relevant reactions such as synthesis of organometallic molecules and polymers, meta-alkylation of aromatics and/or stereospecific hydrogenations. It is this wide diversity of reaction mechanisms that will allow catalytic antibody sensors to detect the presence of an extremely large number of analytes by a variety of transducer methods.

The conditions for reaction and subsequent detection of analytes are as broad as those which allow the formation of antibody-reactant complex. It will be appreciated that these conditions may vary depending on the particular reactant and the particular antibody which is employed. For example, one set of conditions suitable for complex formation includes solution phase and emulsion reaction systems which employ a protic solvent, preferably water, maintained at a pH value between pH 3.0 and 10.0 and at a temperature between 4° C. and 60° C. Catalysis may be carried out at reduced or elevated pressures, but usually is performed at ambient pressure. In addition to solution phase and emulsion reaction systems, suitable conditions also include the use of support materials to which the antibody is physically or chemically bonded. Such support materials are well known to those of ordinary skill in the art as are methods for attaching or immobilizing antibodies to them.

In practice, the reactant(s) is (are) contacted with an appropriate antibody under conditions suitable for the formation of a complex between the antibody and its substrate. The complexed reactant(s) is (are) converted to product(s), and the product(s) released from the complex. Thus, the sensors of the invention are automatically regenerated by the reaction catalyzed in the antibody binding site. In addition, because the catalytic activity found in each antibody may result in a tight binding of the transition state structure, these proteins usually bind transition state analogs far more tightly than the reactants. Consequently, very small concentrations of transition state analog compounds in the assay solution will decrease the catalytic activity of the antibody by binding competitively to the antigen binding site. Accordingly, concentrations of transition state analogs can be determined by monitoring a decrease of the antibody catalyzed reaction rate in the presence of a known quantity of substrate.

Transducers

The transducers used in prior art biosensors generally fall into three basic categories: electrochemical; optical; and physical. The transducers used in the invention likewise fall into the same three basic categories. These include calorimetric, piezoelectric, amperometric, optical fiber, optical waveguide, lipid membrane, potentiometric and electrochemical capacitance/impedance devices. These transducers are described below as they are used in sensing systems incorporating noncatalytic antibodies, enzymes and protein receptors. However, it will be understood that these same transducers and the principles of their operation are applicable with catalytic antibodies in the sensing systems of the invention.

Electrochemical transducers include those having enzyme electrodes (5, 6), immunochemical-mediated ion transport electrodes (7a), and electrochemically-linked immunochemical electrodes. Enzyme electrodes typically consist of an enzyme-containing layer on the surface of either a potentiometric ion-selective or redox electrode or an amperometric electrode. The detection of either the consumption of a reactant or the formation of a product of the enzymatically catalyzed reaction forms the basis for the detection of enzyme substrates.

A typical example is the glucose sensor in which glucose oxidase, which is immobilized in a gel matrix on the surface of the detector, catalyzes the oxidation of glucose according to the reaction:

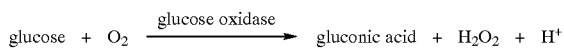

$$\text{glucose} + O_2 \xrightarrow{\text{glucose oxidase}} \text{gluconic acid} + H_2O_2 + H^+$$

An amperometric electrode can be employed to sense either the depletion of oxygen or the production of hydrogen peroxide in order to detect changes in the concentration of the substrate glucose. A similar electrode can also be used in a potentiometric mode in which the consumption and/or production of electroactive species alters the redox potential of the electrode. The electrode material may be any inert metal or other inert conductive material. Platinum, gold and glassy carbon are commonly employed. Alternatively, a potentiometric ion-selective electrode sensitive to hydrogen ions can be employed to detect changes of pH in the enzyme-containing layer to determine the glucose concentration. A variety of chemicals can be detected using analogous sensing mechanisms with different enzymes; however, these enzyme-based detection systems limit the number of chemicals which can be detected to those for which stable enzymes are available. Nevertheless, the same transducing devices may be used in the catalytic antibody sensing systems of the invention without encountering the limitations associated with enzyme systems, the difference being that catalytic antibodies are used in place of the enzyme.

Immunochemical-mediated ion transport electrodes are based on well known ion-selective electrodes. These electrodes rely on hydrophobic ionophores to facilitate the solution of hydrophilic ions into a low dielectric medium, often a plasticized PVC membrane. The ionophores are either macrocyclic or acyclic but form cyclic structures upon complexation with specific ions. Natural antibiotics such as nigericin and valinomycin are often employed as ionophores. Ion-selective electrodes based on these sensing mechanisms are well established in the literature (7b) and are now used for greater than 50% of the clinical assays of sodium and potassium ions (8). These sensors use an antigen-labeled ionophore in a low dielectric membrane in a configuration similar to an ion-selective electrode (7a). The ionophore allows a relatively small exchange current density of several ionic species across the membrane-solution interface. Binding of the antibody to the antigen changes the exchange current density of each ionic species differently, resulting in a change in the mixed-potential at the interface.

In one example of an immunoelectrode biosensor, the antigen is the drug digoxin which is coupled to the ionophore benzo-15-crown-5 (7a). The electrode is used to detect antibodies to digoxin which bind to the digoxin antigen at the surface of the membrane and which affect the kinetics of ionic transport across the interface, altering the equilibrium potential. The electrode may also be used in a competition assay to detect digoxin. Detection limits for the antibody are in the μg/ml range and for digoxin are in the nM range.

Electrochemically linked immunochemical sensors have been discussed in the literature but a reliable sensor which relies on the direct detection of immunochemical reactions as the mechanism for operation has not been described. In one example of such an immunochemical sensor, enzyme-linked electrodes have been employed in which an enzyme-labeled antibody supplies electroactive species for either potentiometric or amperometric detection (9).

Still another example of an immunochemical electrode is the immunochemically sensitive field effect transistor (IMFET) (10,11,12). This detection scheme relies on the ability of a field effect transistor to measure changes in the interfacial charge at the membrane-solution interface, thus allowing measurement of ionically charged antigen or antibody binding at the interface.

Capacitance of impedance transducers are known in which the electrochemical impedance of an electrode interface is measured. Either antigen or antibody can be immobilized on the surface(s) of the sensor. When the corresponding antibody or antigen binds to its counterpart, its presence at the interface alters the makeup of the ionic double layer changing the interfacial impedance (capacitance and/or conductance).

Optical transducers (exemplified by optical fiber and waveguide sensors) comprise the second category of transducers and they too are known in the art (13,14). Conceptually optical fiber sensors are simple. The optical fiber is merely used as a conduit to carry light to and from a miniaturized spectrophotometric cell in which reactant and/or product concentrations are determined either by light absorption, transmission, or fluorescence techniques. Typically, a reversible indicator system (either colorimetric or fluorometric) is trapped inside a semipermeable membrane at the end of the fiber. Sensors for pH (15), pO$_2$ (16), pCO$_2$ (17), and glucose (18) are examples of optical fiber-based sensors.

Alternatively, optical fibers and waveguides can be used in a total internal reflection mode in which the reflected light is altered by changes in a thin layer of the medium surrounding the fiber (e.g., an aqueous sample solution). In this case, the incident and reflected light interact with the surrounding medium via the evanescent field which extends into the surrounding medium from the surface of the fiber, decaying exponentially. The evanescent field extends into the surrounding medium a distance approximately equal to the wavelength of the reflected light. Any absorbing species within the evanescent field can absorb a fraction of the light, causing a decrease in the magnitude of the reflected light. Similarily, fluorophores in the evanescent field region can be excited by the light and the emitted fluorescence efficiently captured by the optical fiber and guided back through the fiber for analysis.

Optical waveguide sensors are used in a manner similar to optical fibers. In this case an optical prism is used to waveguide light rather than an optical fiber. The optical waveguide sensor can be operated either in the evanescent field mode or in the bulk excitation mode in a manner analogous to its optical fiber counterpart.

Optical fibers and waveguides can also be employed to trap light generated by chemiluminescent or electrogenerated chemiluminescent (ECL) reactions, either in the evanescent field or bulk modes of operation. Such ECL transducers offer an extremely sensitive means for detecting ECL-active compounds (TAG) such as, for example, ruthenium trisbypridine, Ru(Bpy)$_3$. Electrochemiluminescent compounds and ECL-TAG assay systems are described in, inter alia, Bard et al. published International Application Serial No. PCT/US85/02153, filed Oct. 30, 1985 and Massey et al. published International Application Serial No. PCT/US87/00987, filed Apr. 30, 1987, which publications are hereby incorporated by reference into this application. Biosensors which couple ECL-TAG systems, catalytic antibodies and optical fiber or waveguide transducers are described in more detail below.

Other types of optical transducers are based on light reflectance techniques. The simplest approach involves monitoring the reflectivity of a smooth surface such as silicon using a p-polarized light beam incident at its Brewster angle. A layer of absorbed or immobilized antibodies results in an increase in the reflectivity and subsequent reaction with antigen results in further reflectivity increases (19). Another approach involves the measurement of surface plasmon resonance using total internal reflection to excite the plasmon in a metal film on a glass prism or diffraction grating (20). The resonance is detected as a sharp minimum in the reflected light at a particular incident angle. Changes in the refractive index of the bathing fluid within fractions of a micrometer from the metal surface result in a change in the critical incident angle. The absorption of proteins (and antigen-antibody binding) at the interface can therefore be detected as a change in the resonance angle.

The third category of transducers is physical transducers. Several detection schemes rely on the measure ment of physical changes such as temperature or mass to monitor biochemical reactions.

Transducer which are based on the principle of measurement of the heat of reaction for a biochemical reaction are known (21). The most common example is the enzyme thermistor pioneered by Danielsson et al. (22) which uses a sensitive thermistor as the transducer to detect temperature changes resulting from enthalpy changes arising from enzyme catalyzed reactions in the vicinity of the thermistor. Enzymatic reactions are characterized by a considerable heat generation, generally in the range of 25–100 kJ/mol. The most straightforward embodiment of the biosensor is the thermal enzyme probe (TEP), in which the enzyme is directly attached to the temperature transducer (a thermistor) either by crosslinking the protein or trapping it in a dialysis tube surrounding the thermistor. Unfortunately, using this geometry, most of the heat generated by the enzymatic catalysis of substrate (analyte) reaction is lost to the surrounding environment and the sensitivity is low. A more efficient arrangement of the components is achieved by employing small columns packed with the enzyme bound to support particles in a flow-through system with the thermistor placed at the exit of the column.

A number of analytes have been detected using the several enzyme sensor devices. The concentration ranges for detection are typically in the range of 0.01 to 10 mM, depending on the enzyme activity and reaction enthalpy. Table I (22) lists the substances analyzed with enzyme thermistors with their concentration ranges.

TABLE I

SUBSTANCES ANALYZED WITH ENZYME THERMISTORS

| Substance | Immobilized enzyme | Concentration range (mmol/l) |
| --- | --- | --- |
| Clinical analysis | | |
| Asorbic acid | Asorbic acid oxidase | 0.05–0.6 |
| AIP | Apyrase | 1–8 |
| Cholesterol | Cholesterol oxidase | 0.03–0.15 |
| Cholesterol esters | Cholesterol esterase + cholesterol oxidase | 0.03–0.15 |
| Creatinine | Creatinine iminohydrolase | 0.01–10 |
| Glucose | Glucose oxidase + catalase | 0.002–0.8 |
| Lactate | Lactate 2-monooxygenase | 0.005–2 |
| Oxalic acid | Oxalate oxidase | 0.005–0.5 |
| Oxalic acid | Oxalate decarboxylase | 0.1–3 |
| Triglycerides | Lipoprotein lipase | 0.1–5 |
| Urea | Urease | 0.01–500 |
| Uric acid | Uriease | 0.05–4 |
| Soluble enzyme analysis | | |
| Urea | Urease (soluble) | 0.1–100 units/ml |
| $H_2O_2$ | Catalase (soluble) | 0.1–100 units/ml |
| Glucose + ATP | Hexokinase (soluble) | 0.1–2.5 units/ml |
| Immunological analysis TELISA | | |
| Albumin (antigen) | Immobilized antibodies + enzyme-linked antigen | –10– 10 |
| Gentamicin (antigen) | Immobilized antibodies + enzyme-linked antigen | 0.1– g/ml |
| Insulin (antigen) | Immobilized antibodies + enzyme-linked antigen | 0.1–1.0 U/ml 0.1–50 g/ml |
| Fermentation analysis and process control | | |
| Cellobiose | β-glucosidase + glucose oxidase + catalase | 0.05–5 |
| Cephalosporin | Cephalosporinase | 0.005–10 |
| Ethanol | Alcohol oxidase | 0.01–2 |
| Galactose | Galactose oxidase | 0.01–1 |
| Lactose | Lactase and glucose oxidase + catalase | 0.05–10 |
| Penicillin G | Penicillinase | 0.05–500 |
| Sucrose | Invertase | 0.05–100 |

However, the number of analytes which may be detected by such enzyme-based thermal biosensors is limited to analytes consumed or generated by chemical reactions for which there are known enzyme catalysts.

The piezoelectric acoustic wave transducer represents another example of transducers which sense changes in physical parameters of the environment. It has been shown that the effect of a thin film on the surface of a piezoelectric crystal effects the resonant frequency of the crystal as if the thin film were an equivalent mass change of the crystal itself (23). Thus, acoustic wave sensors effectively measure the change in mass of a piezoelectric substrate as molecules bind to its surface(s). Bulk acoustic wave (BAW) and surface acoustic wave (SAW) transducers have been employed extensively as gas detectors (24) but only recently have they been used to detect chemicals in fluids (25, 26).

Bulk acoustic wave transducers have been used as gas sensors to monitor the absorption of gas molecules into various coatings on the surface of piezoelectric crystals in many different scientific investigations (24). However, the operation of piezoelectric crystals in a fluid medium has received little attention. Results of investigations of BAW devices in aqueous media in which interfacial chemistries were varied by the deposition of lipid films of stearic acid and also of polyacrylamide gel have been reported (26). It has been demonstrated that the binding of antibody to surface-immobilized antigen affects the harmonic frequency of the system. Therefore, the BAW transducer can be operated reliably in an aqueous environment and the immunochemical reactions on the crystal surface can be detected.

The chemical sensing mechanism which nature employs, namely, receptor proteins embedded in lipid bilayer membranes provides an example of a sensitive and selective chemical transducer (27,28). Specifically, it has been suggested that natural receptor proteins are not necessary for transduction applications and that specific chemical events (e.g., antigen-antibody or enzyme-substrate binding) at the membrane-solution interface can perturb the dipole potential of the lipid headgroups to significantly alter the conductivity of the membrane. In other words, the binding of charged or dipolar species near the interface can alter the electrostatic barrier to ion migration across the membrane. Thus, such lipid bilayer membranes can be used as transducers in the catalytic antibody sensing systems of the invention by embedding catalytic antibodies into or on the surface of the membrane instead of noncatalytic antibodies, receptor proteins, or enzymes to achieve a sensitive and selective biosensor which is rapidly reversible in response to changes in the concentration of an analyte of interest.

In addition to detecting various events associated with the chemical reaction, the transducer is also capable of generating information associated with those events by "transducing" or converting the events into a measurable quantity such as an electronic or optical signal. These signals are then channelled via connections well known in the art to a device which processes the information represented into, e.g., displays, records, and digitized data.

In addition to the transduction mechanisms discussed above, many other analytical chemistry techniques could be employed to detect physical or chemical changes resulting from a reaction catalyzed by a catalytic antibody. Table II lists many of the common analytical techniques that could be thus employed.

TABLE II

Some Commonly Used Analytical Chemistry Techniques

| | |
|---|---|
| ultraviolet and visible absorption spectroscopy | photoacoustic spectoscopy |
| | Raman spectoscopy |
| infrared absorption spectroscopy | atomic absorption spectroscopy |
| fluorescence spectroscopy | atomic fluoresence refractometry |
| atomic emission spectroscopy | optical rotatory dispersion |
| plasma emission spectroscopy | nuclear magnectic resonance (NMR) spectroscopy |
| polarimetry | |
| circular dichroism | X-ray fluorescence spectroscopy |
| electron spin resonance spectroscopy | |
| X-ray diffraction | electron diffraction |

Some Commonly Used Analytical Chemistry Techniques

| | |
|---|---|
| X-ray photoelectron spectroscopy (XPS) | neutron activation analysis |
| | secondary ion mass spectrometry |
| mass spectrometry | |
| electrochemical potentiometry | electrogravimetry |
| eletrochemical polarography | electrochemcial voltammetry |
| electrochemical conductimetry | thermogravimetry |
| differential thermal analysis | differential scanning calorimetry |
| liquid chromatography | column chromatography |
| high performance liquid chromatography (HPLC) | adsorption chromatrography |
| | reverse phase chromatography |
| partition chromatography | ion-exchange chromatography |
| liquid-liquid chromatography | gel chromatography gas-liquid |
| chromatography | thin-layer chromatography |
| paper chromatography | electrophoresis |
| electrochromatography | chemiluminescence |
| electrogenerated chemiluminescence | Auger spectroscopy |

Means for Processing Information Generated by the Transducer

Devices used to process the information generated by the transducers are well known in the art. The particular device used depends on the type of physical or chemical phenomenon being detected. Electrochemical, calorimetric and lipid bilayer membrane transducers are often coupled with electrometers, voltmeters, impedance analyzers and capacitance bridges. Photomultiplier tubes, photodiodes, phototransistors, spectrophotometers, monochromators, and photon counters are among the devices commonly used to process information generated by optical and ECL transducers. Frequency counters and delay-line oscillators are devices often used with piezoelectric transducers.

Specific Embodiments of the Invention

The sensing systems of the invention incorporate catalytic antibodies. The catalytic antibodies used in the sensing systems and methods of the invention may be released into the test environment as free floating particles or may be immobilized on a surface of the transducer or on a separate surface which is associated with the transducer. Preferably, the catalytic antibody is immobilized using techniques well known in the art (29), which techniques generally include any one of four different methods (or combinations thereof): adsorption; entrapment; crosslinking; or covalent bonding. For example, in sensing systems wherein the transducer is a lipid membrane device, the catalytic antibody or antibodies are immobilized into or onto the lipid membrane. In systems wherein the transducer is an electrode or probe, the catalytic antibody may be immobilized or trapped on a spacer material such as, for example, a piece of filter paper which is sandwiched between the sensing membrane of the electrode or probe and a dialysis membrane which is fitted and secured over the tip of the electrode or probe. In a number of the sensing systems, the catalytic antibody may be immobilized on a suitable gel matrix (e.g., polyacrylamide, collagen or crosslinked protein), a silicon wafer, a polymer, an oxidized metal surface or other nonconductive surface. Other immobilization schemes include crosslinking, silane coupling and immobilization in vesicles, micelles and reverse micelles.

In one embodiment of the invention, a potentiometric catalytic antibody biosensor may be used to detect physical or chemical changes in an environment as a result of a chemical reaction taking place in that environment. One such reaction is the hydrolysis of methyl p-nitrophenyl carbonate (MpNPC), a reaction which is catalyzed by a known catalytic antibody. The hydrolysis of each MpNPC molecule produces two hydrogen ions causing a change in the reactive environment, namely, lowering of the pH. The reaction is as follows:

Scheme I

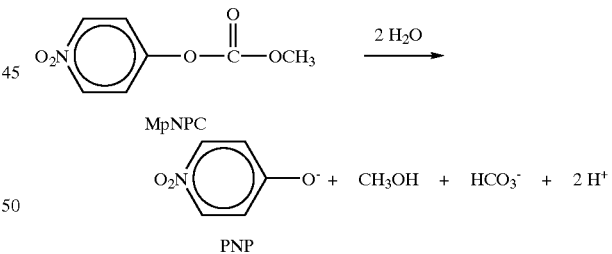

A catalytic antibody specific for the above reaction can be synthesized, as described in Example 1 below, so that the antibody catalyzes the reaction. The catalytic antibody so produced, antibody 48G7, is incorporated into the potentiometric biosensor.

In the potentiometric biosensor, a pH electrode (an ion-selective electrode) is used as the transducer to sense and measure the pH change resulting from the hydrolysis. FIG. 1 shows a pH electrode sensor according to the invention. Glass tube 10 comprises the body of the sensor. The 48G7 antibody is immobilized or trapped on a spacer material 12, preferably a filter paper, located behind a first membrane 14 on the surface of a pH sensitive glass membrane 16 so that the first membrane and the pH sensitive glass membrane form a sensing area 18. Preferably, first membrane 14 is a dialysis membrane. First membrane 14 is secured to the end of the glass tube with securing ring 20. The securing ring may be an O-ring or silicone rubber tubing. Glass tube 10 is filled with a solution 22 (e.g., 0.1M HCl) into which is immersed an internal Ag/AgCl electrode 24.

When the sensor is placed into a test solution containing MpNPC the solution passes through first membrane 14 and into sensing area 18. The hydrogen ions produced as a result of the hydrolysis catalyzed by 48G7 in sensing area 18 diffuse toward pH sensitive glass membrane 16 (as well as away from the glass membrane). As more hydrogen ions are produced, the concentration rises in the sensing area which creates a diffusion gradient of ions away from the sensing area into the bulk of the solution. A steady state is reached in which the rate of diffusion out of the sensing area is equal to the catalytic production rate. The rate of hydrogen ion production is proportional to the concentration of the substrate MpNPC, and thus, the steady state pH at the pH sensitive glass membrane is an indicator of the substrate concentration. Based upon stoichiometric considerations, information generated by the pH electrode can be processed to calculate the concentration of p-nitrophenol (PNP), the other product of hydrolysis, as well as MpNPC. Therefore, in addition to detecting changes in the sensing area, the sensor is capable of quantitatively detecting the presence of an analyte and, because a catalytic antibody is incorporated in the sensor, binding of the antibody to its specific antigen is reversible allowing regeneration of the antibody binding site so that the sensor may be used continuously in subsequent analyses. The use of such a pH-based potentiometric catalytic antibody biosensor is described in more detail in the examples below.

The judicious design and production of a variety of different catalytic antibodies capable of catalyzing reactions of analytes of interest to produce or consume ionic species which can be measured with ion-selective electrodes will make it convenient to assay for many analytes of interest using biosensors of the invention. In accordance with the invention, other potentiometric electrodes can alternatively be employed to measure the potential changes associated with the ion-selective membrane. For example, coated wire electrodes or field-effect transistors or other semiconductor transducers such as those described in Hafeman et al., U.S. Pat. No. 4,591,550, may be used as the transducer for measuring ionic concentration changes.

Figure 2:
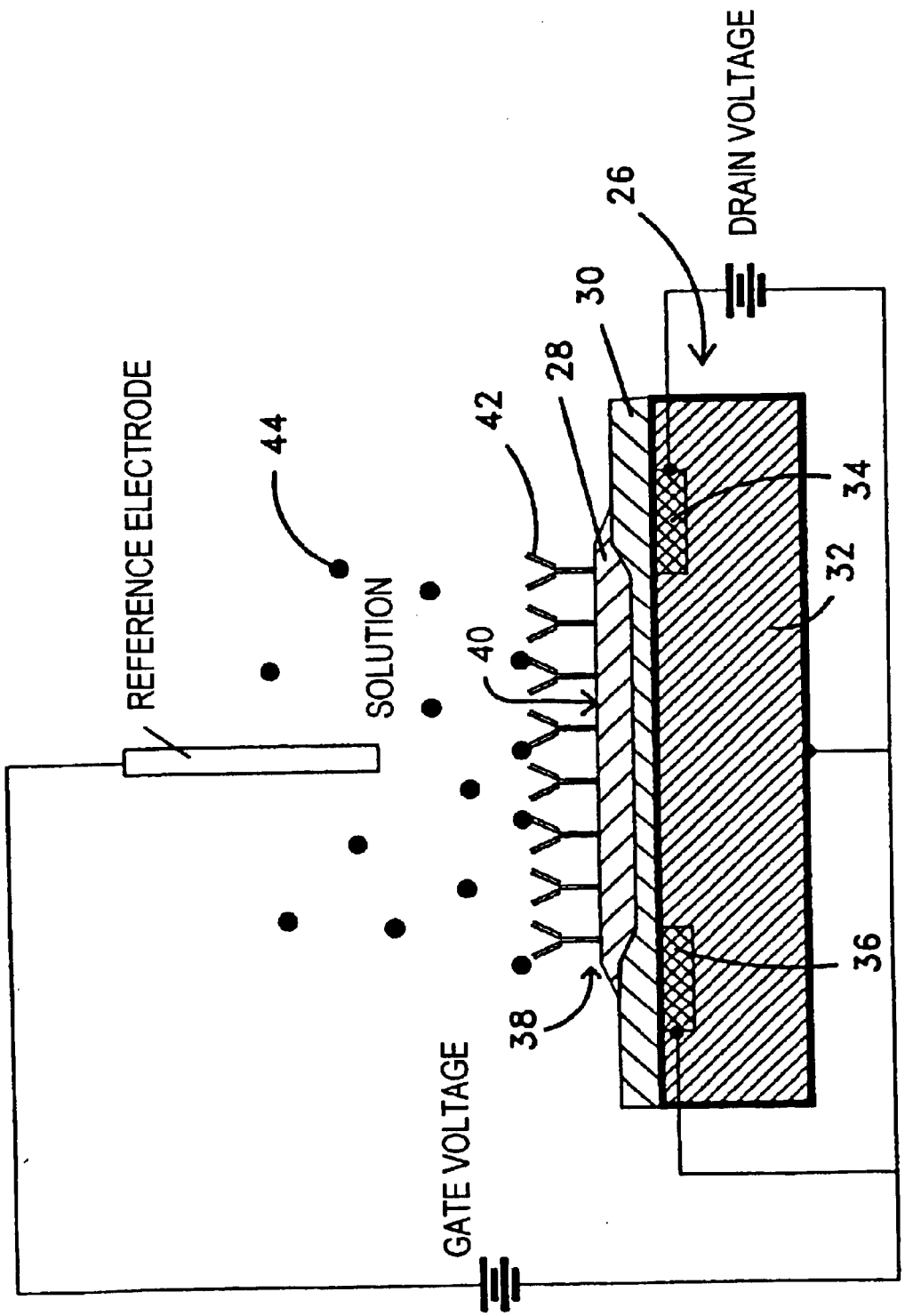
FIG. 2 is a schematic diagram of a catalytic antibody immunochemically-sensitive field-effect transistor.

FIG. 2 shows another type of potentiometric catalytic antibody biosensor according to the invention. The biosensor shown in based on an immunochemically sensitive field-effect transistor (IMFET) which is a charge-sensitive device. The transducer is a solid state gate capacitor 26 comprising a membrane 28 which is affixed to insulator 30 which is in turn affixed to silicon substrate 32. The current flowing from drain 34 to source 36 is modulated by the charge on the solid state gate capacitor 26. Gate area 38 of the gate capacitor is exposed to a solution thereby creating a transistor-solution interface 40. Interface 40 forms an ionic double layer which remains nearly perfectly polarized in aqueous solution. Catalytic antibodies 42 are immobilized at the transistor-solution interface 40. When the catalytic antibodies 42 bind a charged antigen 44 (the analyte, e.g., proteins, polypeptides, many drugs) the net interfacial charge is perturbed and the change can be monitored by the underlying solid state gate capacitor. Thus the solid state gate capacitor 26 is used to monitor changes in the net charge in the ionic double layer formed at the transistor-solution interface 40. Since the antibody is catalytic (i.e., reversible), the antigen is only bound transiently and the charge perturbation will diminish if the analyte concentration returns to its previous value.

Figure 3:
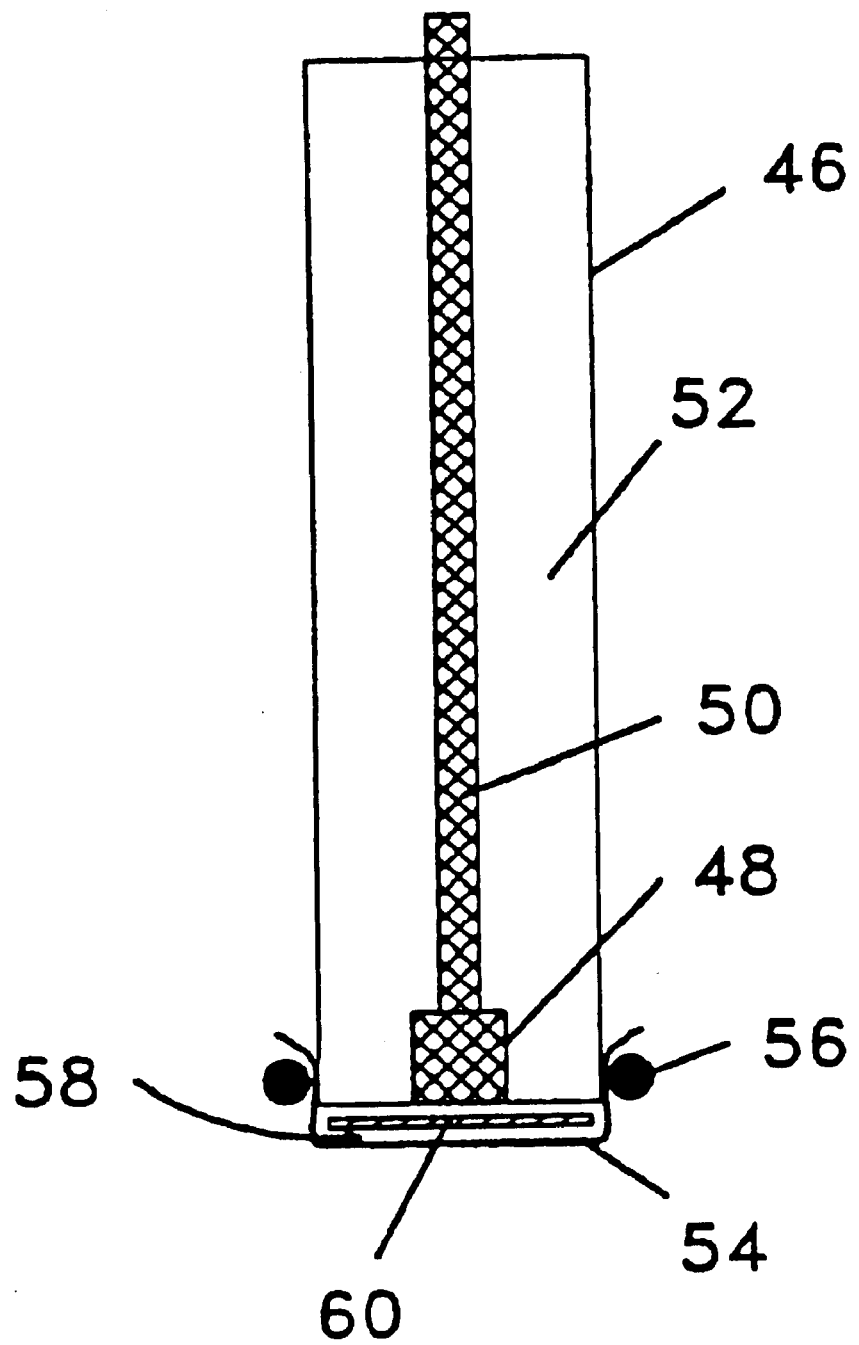
FIG. 3 is a schematic diagram of a catalytic antibody amperometric biosensor.

An amperometric biosensor incorporating a catalytic antibody may also be used to detect an analyte. In FIG. 3, the amperometric biosensor comprises a tubular transducer 46 at one end of which is an electrode 48. Electrode 48 may be any inert metal or other inert conductive or semiconductive material such as, for example, platinum, gold, indium phosphide and glassy carbon. Electrode 48 is connected to a wire 50 which passes through the tubular transducer 46 to a suitable measuring device such as an ammeter. The inside of the tubular transducer is filled with an encapsulation material 52 (e.g., injection molded plastic or teflon) which surrounds electrode 48 and wire 50. The electrode end of tubular transducer 46 is surrounded by dialysis membrane 54 which is held in place by O-ring 56. Sensing area 58 is formed by electrode 48 and dialysis membrane 54. Spacer material 60, e.g., a piece of filter paper, is filled with catalytic antibody and inserted in sensing area 58. The 48G7 antibody, specific for the hydrolysis reaction shown in Scheme I above, may be incorporated into the amperometric biosensor shown in FIG. 3 by trapping the catalytic antibody in spacer material 60. The tip of tubular transducer 46 is then immersed in a solution containing the substrate MpNPC which passes through dialysis membrane 54 into sensing area 58. Catalytic antibody 48G7 trapped on spacer material 60 catalyzes hydrolysis of MpNPC to yield p-nitrophenol (PNP). Thus, the product PNP is detected at sensing area 58 by electrode 48 through oxidation of PNP to the corresponding cation. By holding electrode 48 at the proper oxidation potential for PNP (approximately +0.9V v. SCE). PNP is oxidized to the corresponding cation as follows:

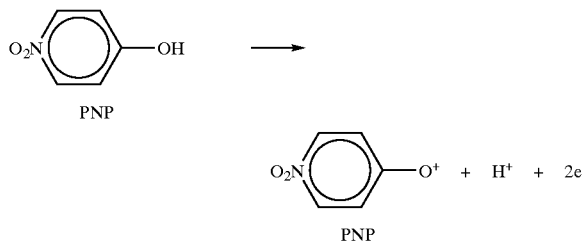

Scheme II

Thus, the production of PNP by the catalytic hydrolysis of MpNPC is monitored by electrode 48 which senses and transduces the oxidation current. The oxidation current is then measured and computed to give the concentration of PNP.

Figure 4:
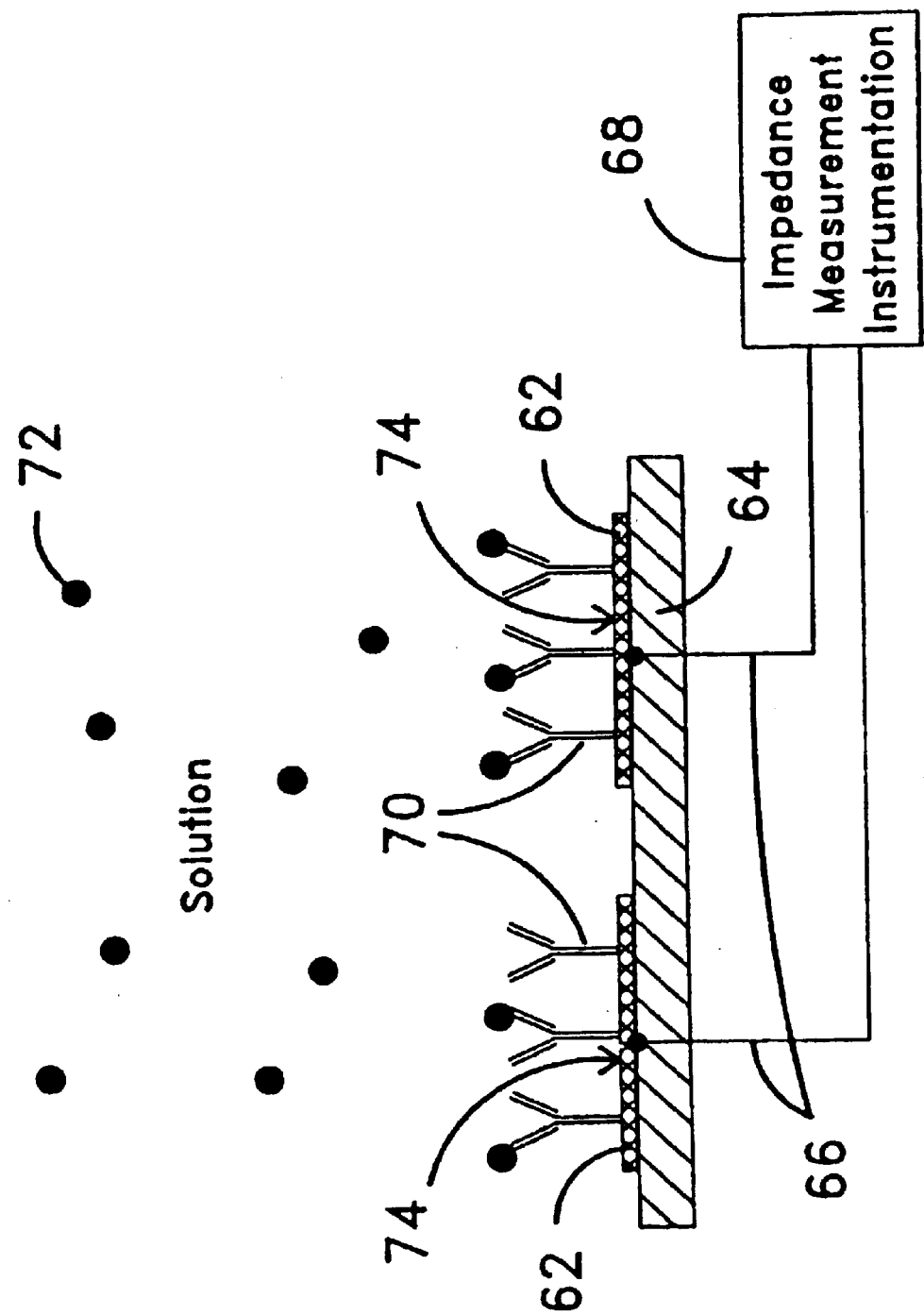
FIG. 4 is a schematic diagram of a catalytic antibody impedance biosensor.

FIG. 4 depicts an impedance (or capacitance) biosensor of the invention. The impedance biosensor comprises electrodes 62 which are affixed to a support material 64. Electrodes 62 are connected by wires 66 to impedance measuring device 68. On the surface of electrodes 62 are immobilized catalytic antibodies 70. Catalytic antibodies are used to transiently bind analytes 72 (antigens) at the electrode-solution interface 74, within the ionic double layer. The presence of the antigen bound to the antibody on the ionic double layer alters the effective dielectric constant of the diffuse double layer, changing the interfacial impedance. The effective dielectric constant can be monitored by a variety of techniques, usually involving application of an ac signal between the electrodes and measurement of the phase angle difference between the voltage and current wave forms. Because the antigen is only bound transiently by the catalytic antibody, the signal is reversed upon return of the antigen concentration to its previous value, i.e., the sensor is reversible.

Figure 5:
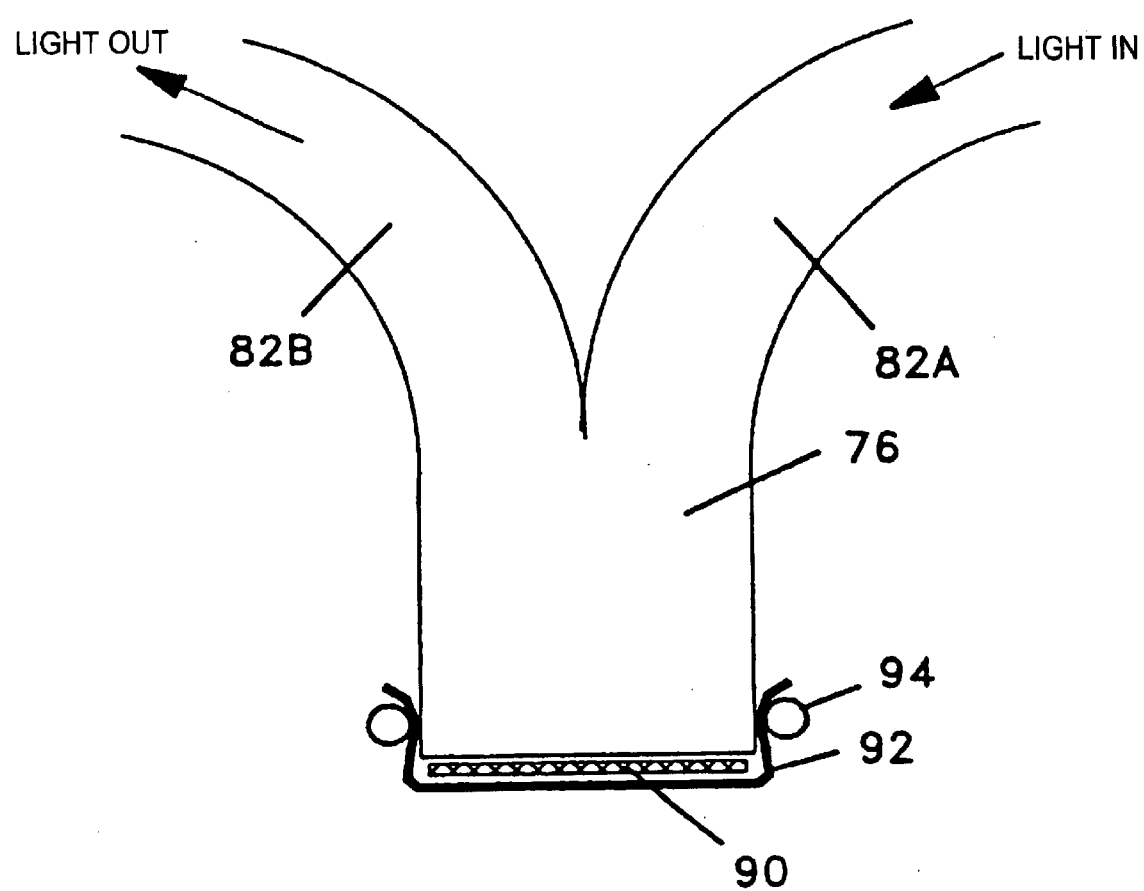
FIG. 5 is a schematic representation of a catalytic antibody optical fiber sensor.

Another embodiment of the invention is an optical fiber-based catalytic antibody biosensor. FIG. 5 is a schematic representation of such an optical fiber sensor and FIG. 6 depicts the sensing system.

Figure 6:
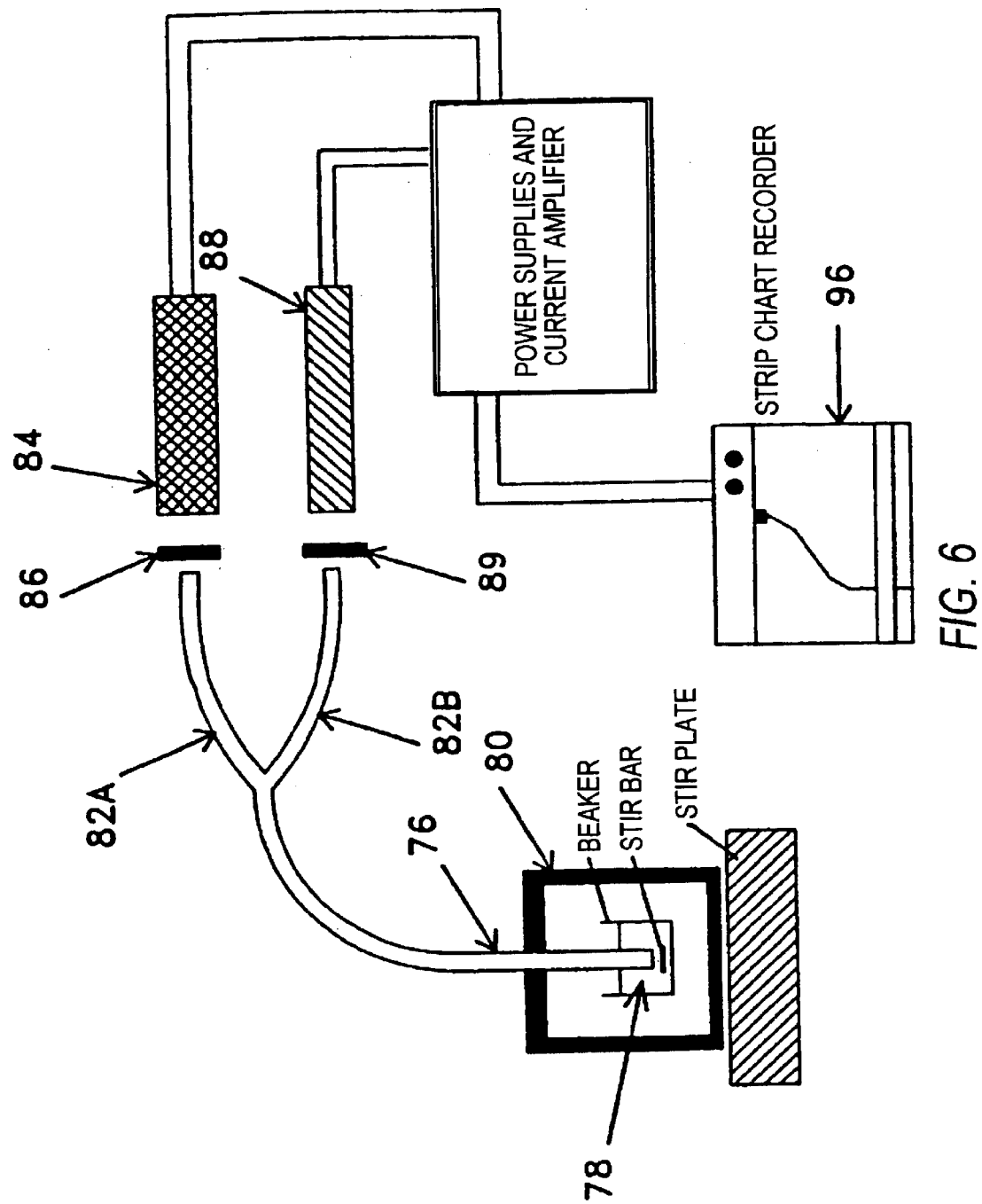
FIG. 6 is a schematic representation of an optical fiber-based sensing system.

Referring to FIGS. 5 and 6, the sensor comprises a randomly dispersed bifurcated fiber bundle 76 which is used to carry light to and from a sample cell 78 in a light-tight enclosure 80. Within the fiber bundle 76 are many excitation fibers 82A which carry light to the sample cell and many return fibers 82B which carry reflected light from the sample cell. Alternatively, two single optical fibers may be used. A light source 84 provides light which is carried to the sample cell via excitation fibers 82A. An example of such a light source is a tungsten lamp. A filter 86 may be placed between excitation fibers 82A and light source 84 which allows only selected wavelengths of light to be transmitted. A photomultiplier tube 88 is used to measure the level of light returned through the return fibers 82B from sample cell 78. A fiber 89 may be placed between return fibers 82B and the photomultiplier tube 88 to limit the light entering the photomultiplier tube 88 to a specific wavelength region for use in sensor systems wherein fluorescence emission or luminescence is being measured, for example. A catalytic antibody is trapped in a piece of filter paper 90 which is held on the end of fiber bundle 76 with a thin dialysis membrane 92. Silicone rubber tubing 94 is used to secure membrane 92 to fiber bundle 76. The catalytic antibody at the end of the fiber bundle 76 catalyzes a reaction to generate a chromophore. The chromophore absorbs a fraction of the light at the end of the fiber, resulting in less reflected light returning to photomultiplier tube 88. These data are transduced to a voltage proportional to light intensity which is recorded by a suitable device such as a strip-chart recorder 96. The data may be then input into a microprocessor (not shown) for analysis and computation of the concentration of the chromophore. This embodiment of the invention is described in further detail in the examples below.

Figure 7:
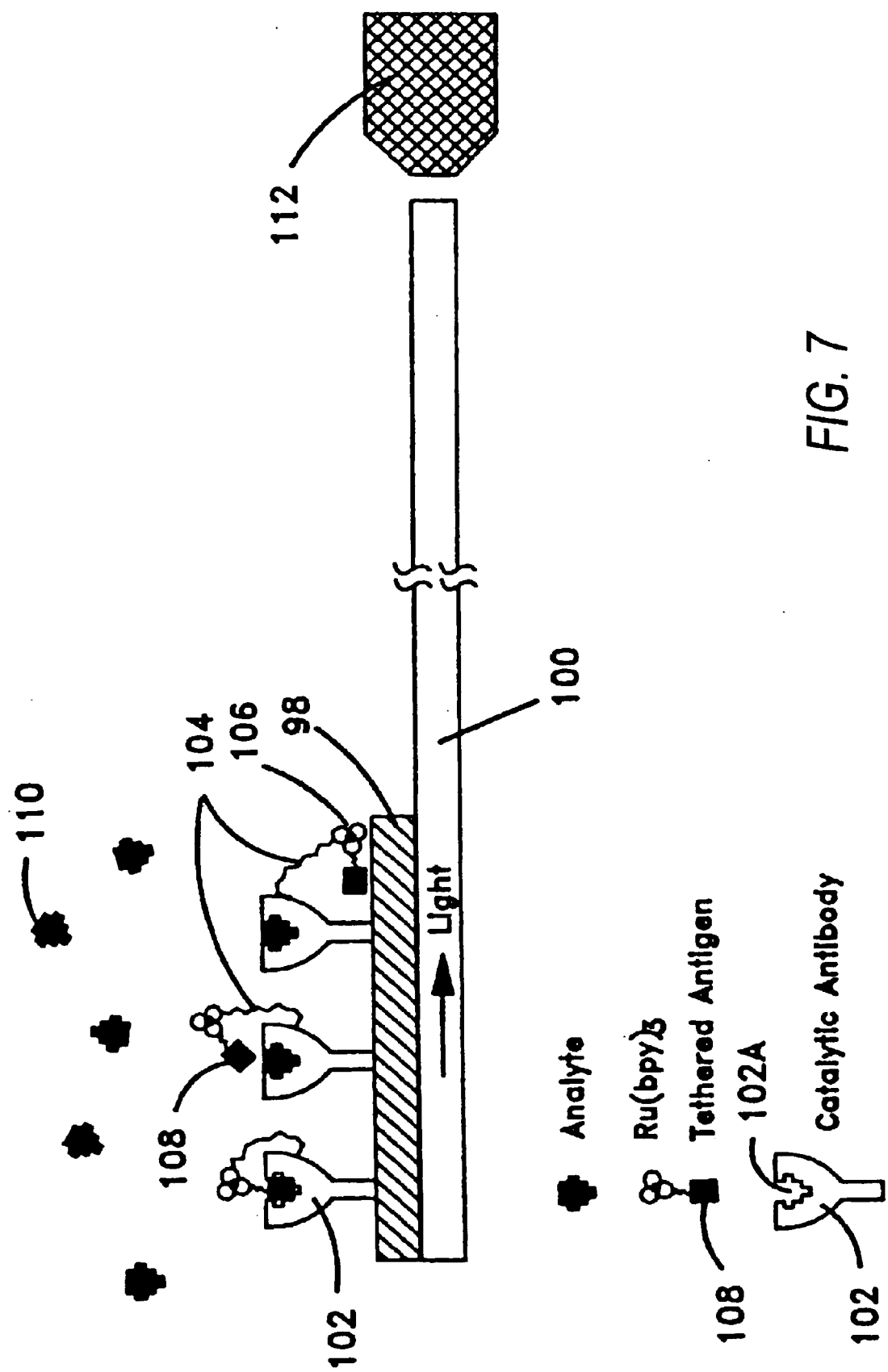
FIG. 7 is a schematic diagram of one configuration of a catalytic antibody electrogenerated chemiluminescent (ECL) biosensor.

The invention also includes a sensitive, selective sensor which couples an ECL-TAG detection system, a catalytic antibody and an optical fiber or an optical waveguide. FIG. 7 shows a configuration of such a sensor. Referring to FIG. 7, a transparent electrode 98 is placed near or on the surface of either an optical fiber or waveguide 100. The electrode surface is preferably any conductive material which can be employed in an ECL-TAG detection system, such as, for example, platinum, gold, glassy carbon, indium-tin-oxide, etc. Catalytic antibodies 102 (or, preferably, the Fab fractions thereof) are immobilized on the surface of the electrode or alternatively to a separate but closely spaced surface (not shown). Antibodies 102 are preferably oriented by the immobilization process so that the antigen binding sites 102A are oriented away from the electrode surface. Covalently attached to the antibody (or to any other nearby surface or molecule) through a linker arm 104 is a bifunctional molecule consisting of an ECL-active moiety (TAG) 106 tethered to an antigen or hapten, tethered antigen or hapten 108, which is weakly bound to the antibody in antigen binding site 102A. Light is produced by an ECL reaction. For example, the TAG may be ruthenium trisbipyridine, Ru(Bpy)$_3$. Tethered antigen or hapten 108 is designed such that is bound to catalytic antibody 102 with a weaker bind affinity than analyte 110. In the absence of analyte 110 (which has a larger binding equilibrium constant than the tethered antigen 108) tethered antigen or hapten 108 is bound in antigen combining site 102A and TAG 106 is rendered electrochemically and ECL inactive. In the presence of analyte 110, the tethered antigen or hapten 108 is rapidly displaced through competition for binding site 102A, and freed TAG 106 becomes electrochemically and ECL active. Freed TAG 106 participates in the ECL process at electrode 98 by creating photons in the vicinity of the electrode. A portion of the light produced by the ECL reaction is caught by optical fiber or waveguide 100 and routed from the sensing area of the sensor out of the sensing environment to external light measuring instrument 112, such as, for example, a photomultiplier tube. Because TAG 106 is not consumed in the ECL process, it is free to continually generate photons though the ECL process as long as it is not bound to antibody binding site 102A. In order to maintain the sensor in a probe-type configuration, the light measuring instrument 112 should either be part of the sensor (e.g., a photo sensitive solid state diode or transistor integrated in a semiconductor substrate, not shown) or else the light should be guided from the probe to light measuring instrument 112 through either waveguide or optical fiber 100.

Preferably, the antibody should catalyze some reaction of the analyte so that the analyte will be rapidly released from the binding site. This will allow the tethered antigen or hapten to recombine with the antibody when the analyte concentration decreases. The catalytic antibody employed should not catalyze any reaction with the tethered antigen so that the tethered antigen is not altered during the detection process. The tethered antigen should also preferably be designed to have a lower binding constant than the analyte so that the tethered antigen will be displaced by the analyte.

The invention also includes a calorimetric biosensor employing catalytic antibodies as the molecular recognition element. Catalytic antibodies are employed to selectively catalyze the reaction of some analyte of interest:

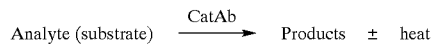

Figure 8:
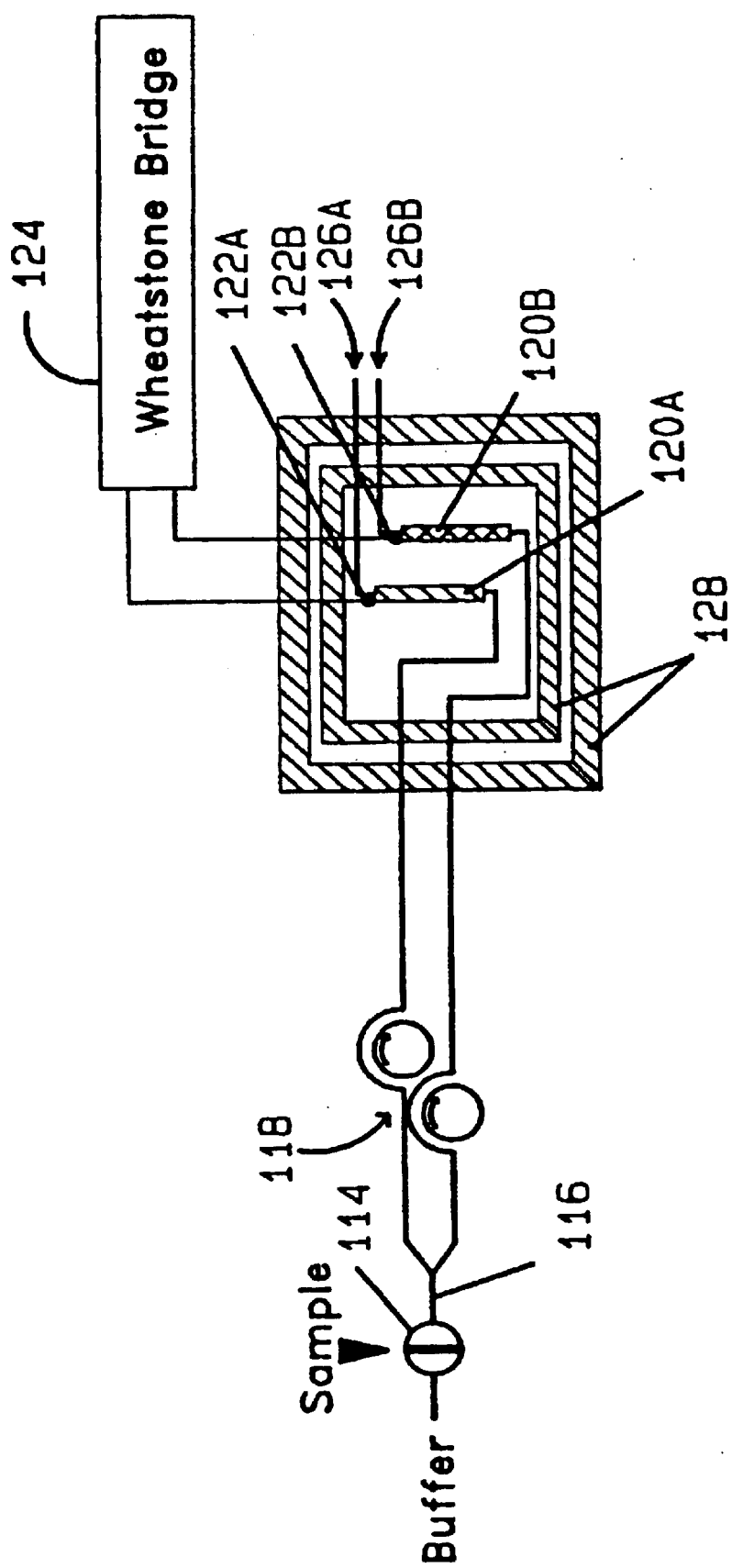
FIG. 8 is a schematic diagram of a catalytic antibody calorimetric biosensor.

The reaction catalyzed may generate heat (exothermic reactions) or absorb heat (endothermic reactions). A temperature transducer is used to detect the heat generated or absorbed by the reaction. The presence of an analyte of interest may be detected calorimetrically based on the heat of the reaction which produces or consumes the analyte. The transducer may be any one of the well known temperature transducers, such as, for example, thermocouples, resistance temperature detectors, integrated circuit temperature detectors or thermistors. Preferably, the catalytic antibody is immobilized on or near the surface(s) of the temperature transducer so that the sensor may be used as a probe-type biosensor. A representative calorimetric biosensor system according to the invention is shown in FIG. 8. The system comprises sampling valve 114 which is connected to inlet 116 which is in turn connected to two-channel pump 118. Pump 118 is connected to a pair of columns 120A and 120B. Column 120B is packed with a catalytic antibody which catalyzes the reaction of the analyte of interest and which is immobilized within the column. Column 120A does not contain the catalytic antibody and is used as an internal reference. Thermistors 122A and 122B are attached at the ends of columns 120A and 120B, respectively. Each of thermistors 122A and 122B are electrically connected to wheatstone bridge 124. Waste outlets 126A and 126B are also attached to each of columns 120A and 120B, respectively. Double wall plexiglass housing 128 surrounds columns 120A and 120B. Housing 128 is immersed in a thermostated water bath (not shown). In operation, a carrier buffer solution is fed through sampling valve 114 into inlet 116 and then is pumped by means of two-channel pump 118 through the two columns 120A and 120B and out to waste outlets 126A and 126B. A solution containing the reactants of the reaction to be catalyzed is injected into the carrier buffer solution through sampling valve 114 and is then pumped through the system as described above. As the sample solution is pumped into column 120B, the catalytic antibody immobilized on the column catalyzes the reaction which generates or consumes heat. The heat is detected by thermistor 122B which transduces the heat change along electrical connections to wheatstone bridge 124. The solution then passes out of column 120B through waste outlet 126B. Wheatstone bridge 124 is connected to an electrometer (not shown) which is used to monitor the differential resistance between output from thermistor 122B and thermistor 122A on reference column 120A. The analog output of the electrometer is monitored using a microprocessor (not shown) which then processes the input data to give the concentration of the analyte of interest.

Figure 10:
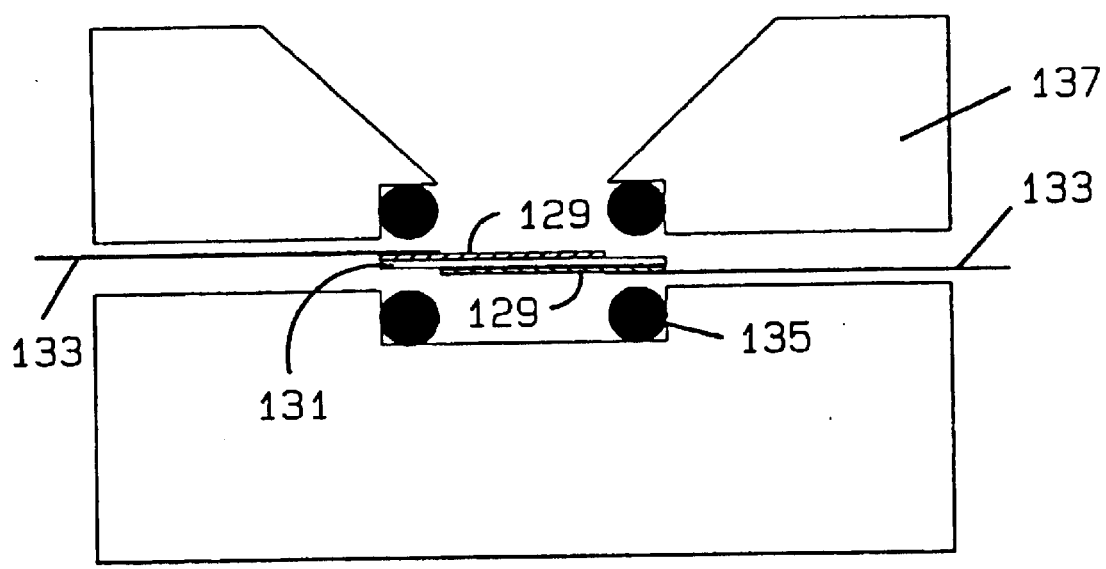
FIG. 10 depicts a plexiglas housing used for mounting crystals in a catalytic antibody BAW biosensor.

In another embodiment of the invention, catalytic antibodies are employed as selective and reversible molecular recognition elements in piezoelectric chemical sensors. FIG. 9 shows a bulk acoustic wave (BAW) chemical sensor. FIG. 10 shows a plexiglas housing used for mounting piezo electric crystals. Referring to both FIGS. 9 and 10, aluminum electrodes 129 are affixed to the top and bottom of quartz crystal 131. Foil 133 provide electrical connections to crystal 131. Foil 133 may be any conductive material such as platinum or silver. Crystal 131 is held with silicone O-rings 135 in plexyglass housing 137. Catalytic antibodies (not shown) are immobilized on aluminum electrodes 129 either in polyacrylamide gel or directly to the aluminum by known methods (26). Use of the BAW chemical sensor is further described in the examples below.

In still another embodiment of the invention, catalytic antibodies are incorporated in lipid bilayer biosensors to achieve a sensitive and selective biosensor which is rapidly responsive to changes in the concentration of an analyte of interest. The catalytic antibody lipid-bilayer is based on a planar bilayer lipid membrane (BLM) upon which or in which are immobilized catalytic antibodies or modified catalytic antibodies. The catalytic antibody binds specifically to the analyte of interest from the bathing solution. The presence of the analyte at the membrane-solution interface perturbs the structure of the interface, resulting in a change energy barrier to the flow of ionic species across the membrane, i.e., changing the ionic permeability and the electrical impedance. Because the antibody catalyzes the reaction of the analyte to a species which is not tightly bound, the analyte is only bound momentarily by the antibody and the response of the system is reversible, i.e., the lipid-bilayer membrane sensor responds to decreasing as well as increasing analyte concentrations.

Figure 11:
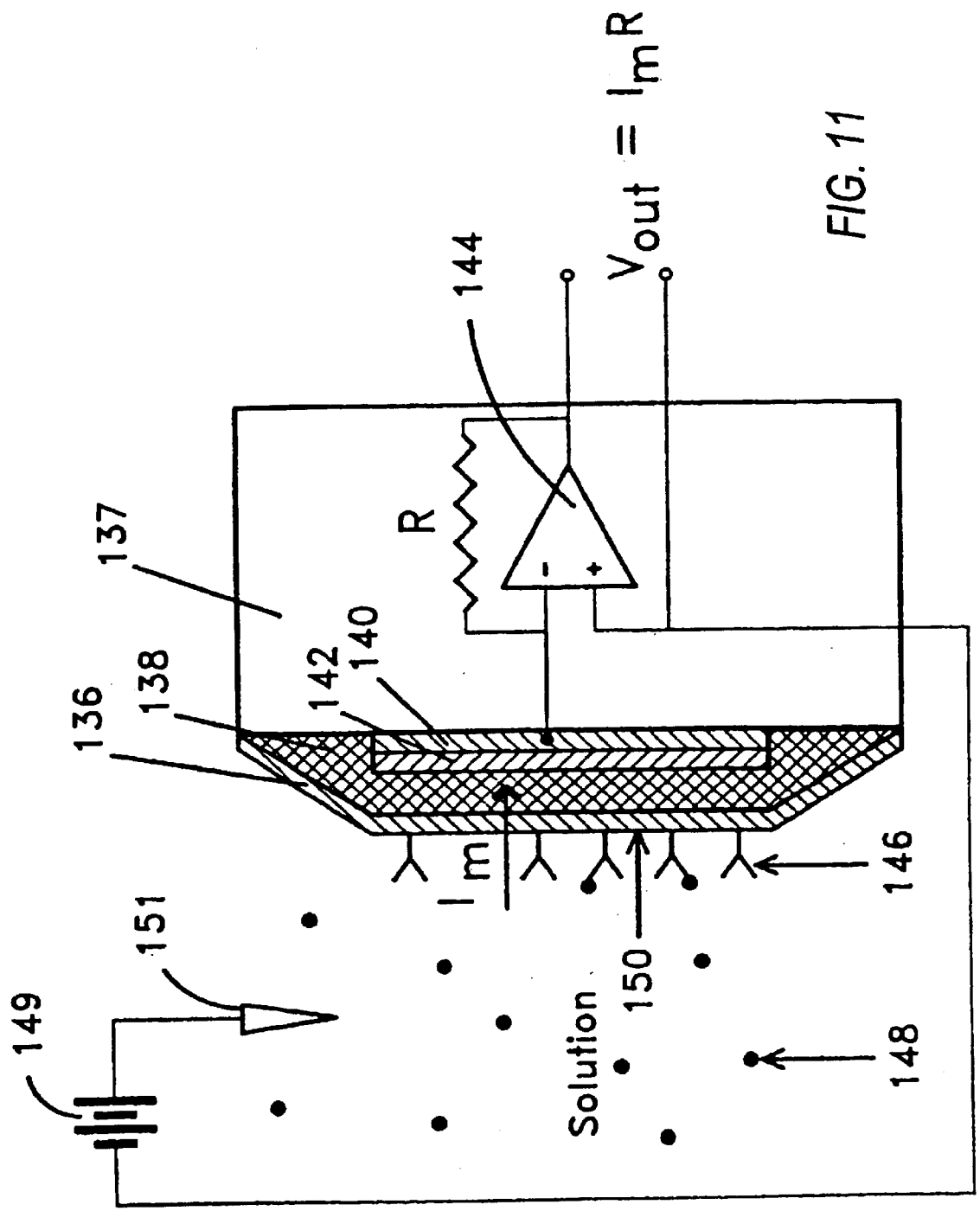
FIG. 11 is a schematic representation of a catalytic antibody lipid-bilayer biosensor.

The lipid-bilayer biosensor according to the invention is preferably configured as shown in FIG. 11. The BLM 136 is deposited using the Langmuir-Blodgett technique or by self assembly techniques on the surface of a hydrogel support 138. These techniques are known in the art (30). Hydrogel supports are used because they provide support yet maintain an aqueous environment for the BLM. Insulating substrate 137 is coated with a thin film of silver 140. Top surface 142 of film 140 is chloridized to yield a film of AgCl, thereby creating an Ag/AgCl quasi-reference electrode to measure conductivity changes. An external current amplifier 144 is employed to amplify the transmembrane current, $I_m$, which flows through the membrane in response to a small voltage perturbation applied to the membrane by a voltage source 149 attached to a reference electrode 151 in the bathing solution. Preferably, the current amplifier is integrated into the insulating substrate 137 using microfabrication techniques. In order to avoid the ionic concentration gradients which dc potentials would cause, either ac or pulsed dc perturbation potentials are preferably used.

Catalytic antibodies 146 are anchored to the BLM 136. Charged or dipolar analytes (antigens) 148 bind to the catalytic antibodies 148 close to the solution-membrane interface 150. In order for the analyte 148 to affect the ionic conductivity of BLM 136, it is important that it approach as close as possible to interface 150 so that ionic and dipolar interactions with the lipid molecules in BLM 136 can perturb its structure. The output of the current amplifier 144, $V_{out}$, is proportional to the transmembrane current, $I_m$. The binding and hydrolysis of an analyte 148 by the catalytic antibody 148 at the surface of the lipid bilayer membrane 136 perturbs the physicochemical properties of the membrane (e.g., by dipole-dipole, charge-charge, and/or charge-dipole interactions or partition of reaction products into the lipid membrane) which alter the transmembrane current. Thus, the output of the current amplifier indicates the presence of the analyte in the bathing solution. Alternatively, if substrate is included in the bathing solution, the presence and/or concentration of inhibitors of the catalytic properties of the catalytic antibody are also detected.

Figure 12B:
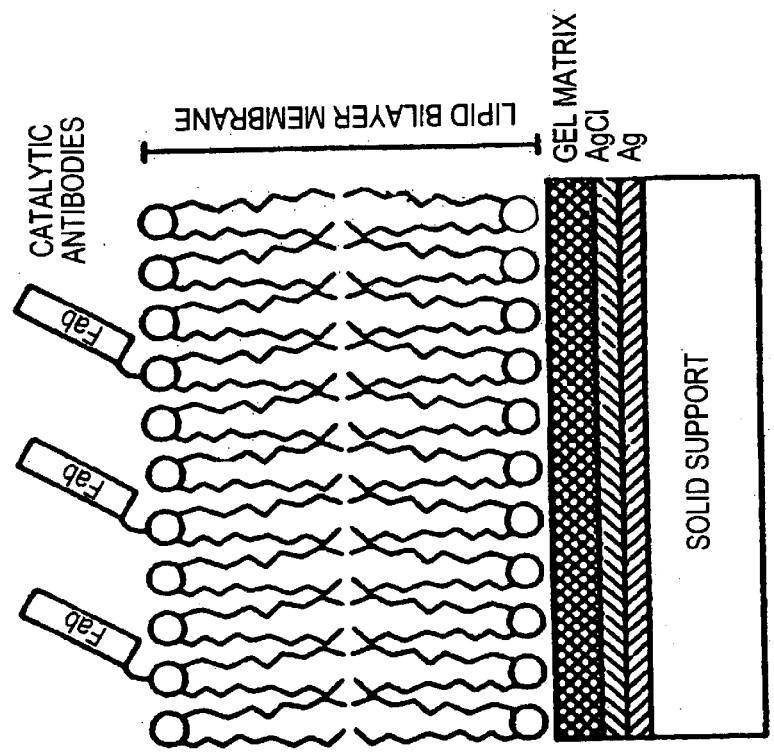
FIGS. 12A–D show schematic representations of possible configurations for catalytic antibodies immobilized to a lipid-bilayer membrane; (A) catalytic antibodies covalently immobilized to natural or synthetic lipids; (B) Fab fragments of catalytic antibodies immobilized to lipids; (C) Fab fragments of catalytic antibodies covalently attached to membrane associated domain of a second protein; and (D) Fab fragments of catalytic antibodies covalently bonded to synthetic hydrophobic polypeptide.
Figure 12A:
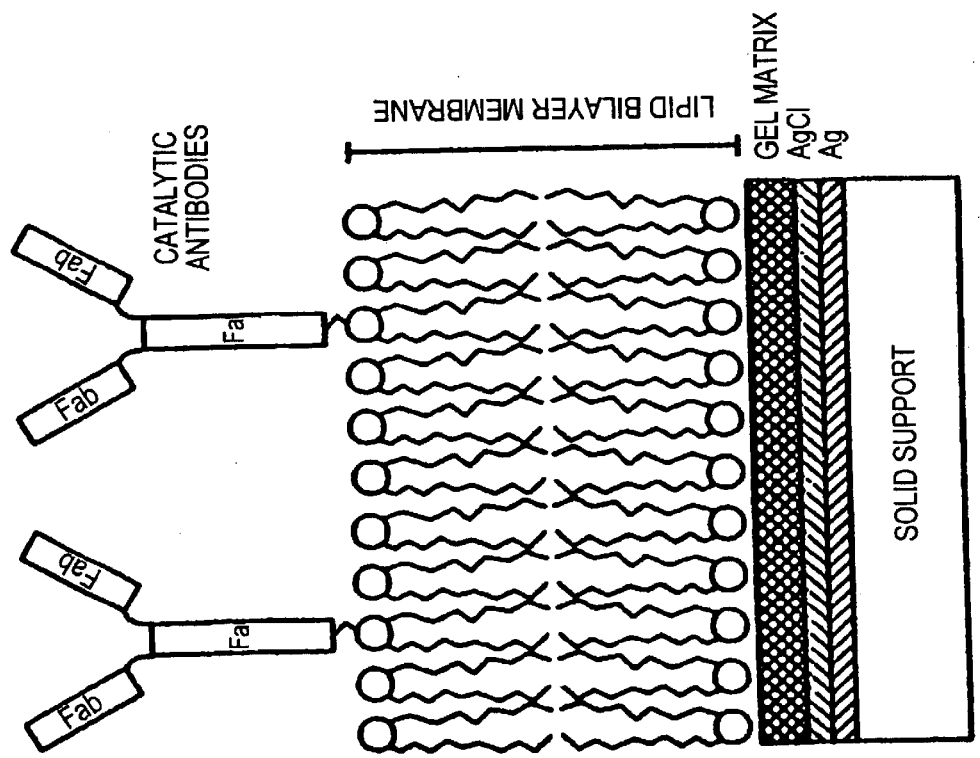
Figure 12D:
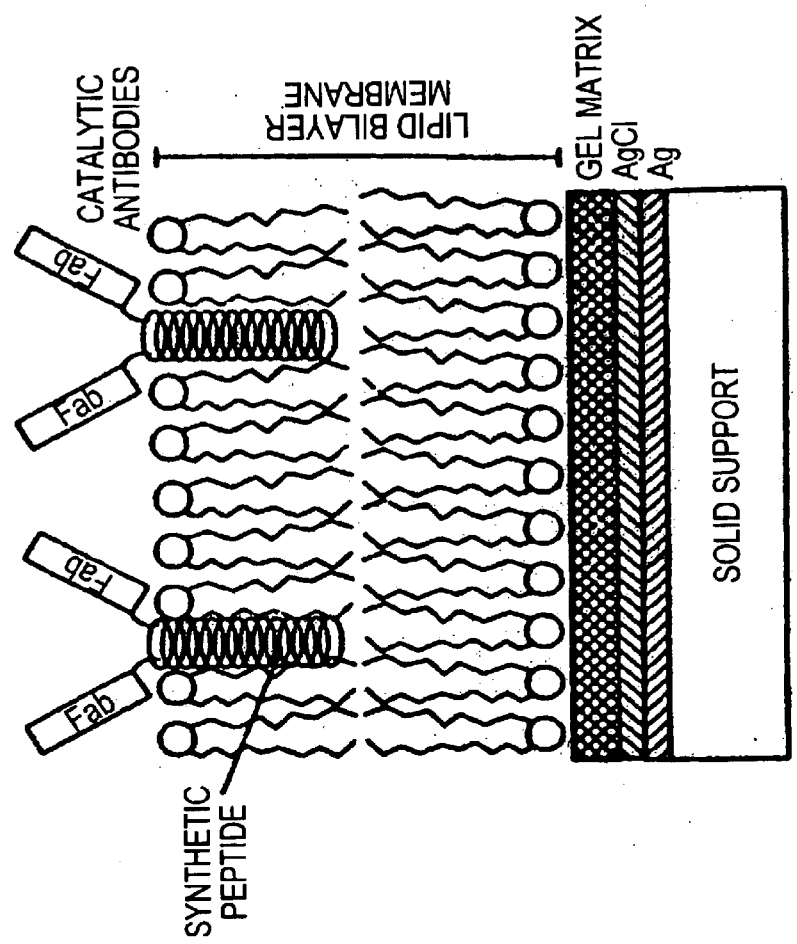
Figure 12C:
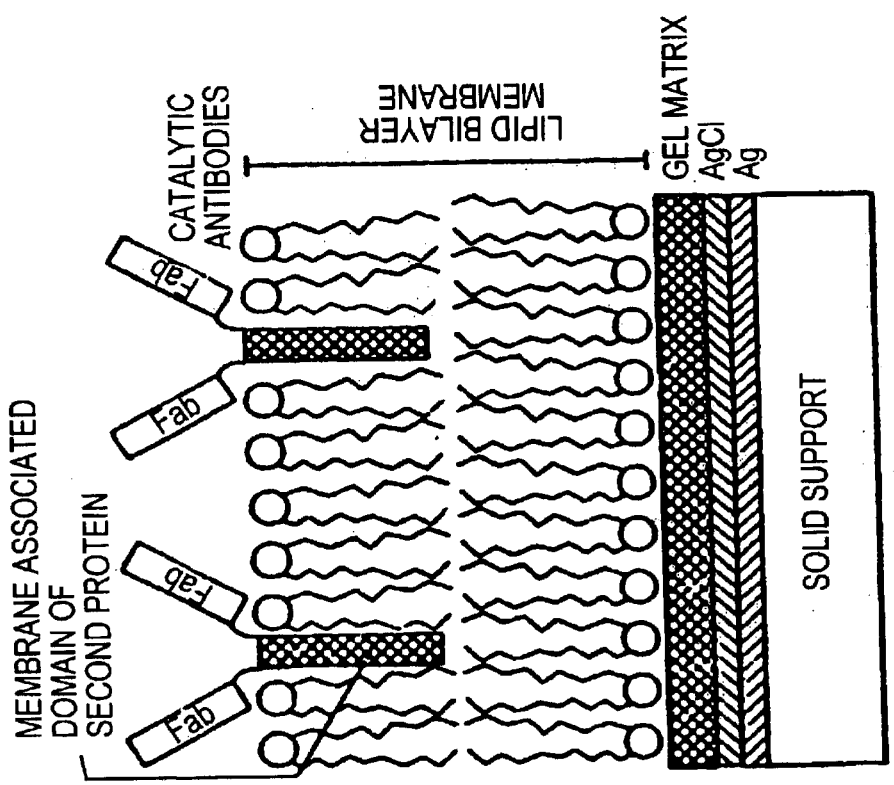

A variety of methods are used to anchor the catalytic antibody to or in the lipid-bilayer membrane as shown in FIGS. 12A-D. In FIG. 12A, the catalytic antibodies are shown covalently attached to lipid molecules which may be specifically synthesized to allow such immobilization. FIG. 12B shows a similar configuration except that only the Fab fraction of the catalytic antibody is immobilized to minimize the distance between the binding site and the interface. Alternatively, catalytic antibodies may be covalently attached to a natural or synthetic protein molecule in the membrane. In FIG. 12C, the Fab portion of the catalytic antibodies are covalently attached to a membrane-associated domain of a second protein molecule such as rhodopsin which is normally found embedded in cell membranes. The membrane-associated domain may be from either a peripheral- or integral-membrane protein and may completely span the lipid membranes or be embedded in it as shown in FIG. 12C. In FIG. 12D, the Fab portion of the catalytic antibody is covalently attached to a synthetic polypeptide which may be synthesized from hydrophobic amino acids which energetically favor the nonpolar lipid-bilayer interior environment. These configurations are only several examples of many different means by which the catalytic antibody, or portions thereof, may be anchored at the membrane-solution interface.

The sensors according to the invention make possible the detection of either the binding or the catalytic activity of the catalytic antibody. Therefore, sensors can be used to measure the concentration of nearly any molecule which binds to the catalytically active antigen binding site of the antibody. In the presence of an inhibitor, the catalytic activity will be severly diminished and thus, a measure of the catalytic activity inhibited indicates the concentration of the inhibitor.

Accordingly, the invention contemplates a biosensor incorporating catalytic antibodies as the molecular recognition element, which is used to detect the presence and/or the concentration of catalysis inhibitors. For example, a variety of antibodies which bind phosphoryl choline (a transition state analog for the hydrolysis of choline esters) have been identified. In addition, at least one phosphoryl choline binding monoclonal antibody (MOPC167) has been reported to catalyze the hydrolysis of aromatic choline esters (31). Thus, in one embodiment, a pH-based biosensor, shown in FIG. 1, may be used to monitor the catalytic activity of the antibody MOPC167 (Hazelton Laboratories America, Inc., Rockville, Md.) in the presence of choline esters to detect inhibitors of choline esterases and choline ester binding proteins (acetylcholine membrane receptor). Such inhibitors include many neurotoxins which are currently used as chemical and biological warfare agents. The biosensor incorporates the catalytic antibody MOPC167 which catalyzes the hydrolysis of aromatic choline esters:

Scheme III

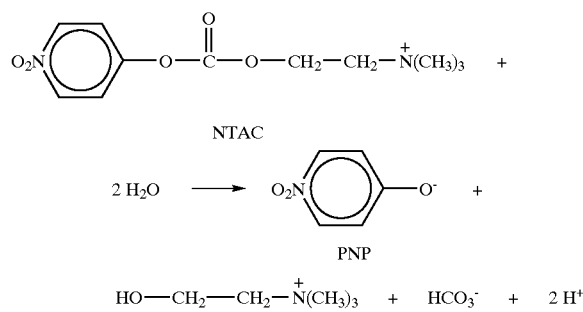

The preparation of antibody MOPC167 is known (32). The antibody MOPC167 binds the aromatic choline ester and energetically stabilizes the transition state structure for the reaction. The reaction products are loosely bound and diffuse from the binding site after hydrolysis occurs, regenerating the catalytic site. The biosensor which employs MOPC167 as its molecular recognition element may be used to detect the presence of molecules which bind to the catalytic site of the antibody.

Referring now to the biosensor shown in FIG. 1, the MOPC167 is trapped on spacer material 12 between the membrane 14 and pH-sensitive glass membrane 16. The tip of the sensor is bathed in a solution containing the aromatic choline ester which diffuses through the dialysis membrane into sensing area 18 containing MOPC167 antibody. The antibody catalyzes the hydrolysis of the aromatic choline ester, producing acid which changes the pH in the sensing area. Measurement of the pH change in the presence of the aromatic choline ester is therefor an indicator of the catalytic activity of the MOPC167 antibody. If a sample containing an inhibitor is added to the bathing solution, it diffuses into the sensing area and inhibits the activity of the antibody so that the pH in the sensing area rises toward the value of the bathing solution. In this manner, the presence and/or concentration of the inhibitor is monitored. Thus, samples may be tested for the presence of inhibitors using catalytic antibody sensors. The biosensor may then be regenerated by bathing it in a buffer solution not containing the inhibitor for approximately 60 minutes. Many other embodiments of the inhibitor biosensor may be envisioned in which different transducers and/or catalytic antibodies are employed.

Preparation of Catalytic Antibodies

Catalytic monoclonal antibodies are prepared by modification of the technique disclosed by Koprowski et al. in U.S. Pat. No. 4,196,265, issued Apr. 1, 1980, which is hereby incorporated by reference. The details of that process are known in the art. A series of monoclonal antibodies directed to a specific reactant are prepared under suitable conditions. This involves first immunizing BALB/C mice with an appropriate antigen. The antigen may be the desired reactant; the desired reactant bound to a peptide or other carrier molecule; a reaction intermediate; or an analog of the reactant, the product or a reaction intermediate. "Analog" as the term is used herein encompasses isomers, homologs or other compounds sufficiently resembling the reactant in terms of chemical structure such that an antibody raised against the analog may participate in an immunological reaction with the reactant but will not necessarily catalyze a reaction of the analog.

Antibody-producing lymphocytes are then removed from the spleens of the immunized mice and hybridized with myeloma cells such as SP2/0 cells to produce hybridoma cells. These hybridoma cells are then plated in the wells of microtiter plates. The series of monoclonal antibodies being produced by the hybridoma cells is screened under appropriate conditions to identify monoclonal antibodies which catalyze the desired reaction under appropriate conditions. Screening may be conveniently accomplished by treating a standardized solution of the reactant with an aliquot of medium withdrawn from a microtiter well and measuring the presence of the desired product by conventional instrumental methods. This measurement may be readily conducted, for example by spectrophotometric methods or by gas-liquid or high pressure liquid chromatography. By comparison with standardized samples of the desired product or reactant, rates of reaction may be quantified. In this manner, wells containing hybridoma cells producing catalytic monoclonal antibodies are identified. The selected hybridoma cells are then cultured to yield colonies.

These colonies may be further propagated in in vitro or in vivo systems. In the latter case, mice such as syngeneic BALB/C mice are inoculated intraperitoneally with the selected hybridoma cells and produce tumors, generally within two or three weeks. These tumors are accompanied by the production of ascites fluid which contains the desired monoclonal antibodies. The monoclonal antibodies are then separately recovered from the ascites fluid by conventional methods such as ultrafiltration, ultracentrifugation, dialysis and immunoaffinity chromatography.

Monoclonal antibodies directed to an antigen which is a known substrate for an enzyme may be prepared and used to increase the rate of conversion of the substrate to the product. This method is useful for example in increasing the rate of conversion of o-nitrophenyl-β-D-galactoside, a known substrate for the enzyme β-D-galactosidase, to o-nitrophenol and β-D-galactose. In this method, a series of monoclonal antibodies to the enzyme are prepared by inoculating BALB/C mice with the enzyme and proceeding according to the general technique described above. The series of antibodies so produced is screened under suitable conditions to identify a first monoclonal antibody which binds to the active site of the enzyme. Such a monoclonal antibody may be identified by screening for antibodies which under appropriate conditions inhibit binding of the antigen (substrate) to the enzyme. This screening process may be conveniently carried out by conventional methods of measuring enzyme binding activity, e.g. radioimmunoassay (RIA). This first monoclonal antibody so identified is separately recovered according to the general technique and is used to innoculate fresh BALB/C mice. By following the general technique a series of monoclonal antibodies to the first monoclonal antibody is produced. The antibodies so produced are termed "anti-idiotype" monoclonal antibodies. The series of anti-idiotype monoclonal antibodies is then screened according to the general method to identify anti-idiotype monoclonal antibodies which bind the antigen (substrate) under suitable conditions and convert it to the product. By "suitable conditions," are meant conditions within the parameters described above for antibody-reactant complex formation. An anti-idiotype monoclonal antibody so produced and separately recovered may be used in accordance with this invention to increase the rate of conversion of substrate to product.

To prepare a monoclonal antibody capable of catalyzing a reaction which is otherwise catalyzed by a cofactor, mice are inoculated with the cofactor bound to the reactant or to an analog of the reactant or product, and the general technique of Koprowski, cited above, is followed. A series of hybridoma cells is then prepared according to the general method and screened for the production of monoclonal antibodies which can complex with free cofactor and reactant, increase the rate of the chemical reaction and release the product. Such a monoclonal antibody directed against indole pyruvic acid-pyridoxamine phosphate imine, for example, selectively increases the rate of conversion of indole pyruvic acid to the amino acid tryptophan. The appropriate cofactor is added to the reaction mixture preferably in an amount at least equimolar to that of the monoclonal antibody.

Methods for generating catalytic monoclonal antibodies for certain reactions are disclosed in Jacobs et al., "Catalytic Antibodies", *J. Am. Chem. Soc.*, 109, No. 7, 2174–2176 (1987) and Napper et al., "A Sterospecific Cyclization Catalyzed by an Antibody", *Science*, 237, 1041–1043 (1987), the disclosure of which references are incorporated herein by reference. An example of the preparation of a catalytic antibody according to Jacobs et al., which is capable of catalyzing a specific hydrolysis reaction is set forth in Example 1.

EXAMPLE 1

Preparation of the Catalytic Antibody 48G7 Capable of Catalyzing the Hydrolysis of p-Nitrophenylcarbonate Monoclonal antibodies were specifically elicited to the tetrahedral nitrophenyl phosphonate transition-state analogue (2) for the aqueous hydrolysis of the corresponding carbonate (1):

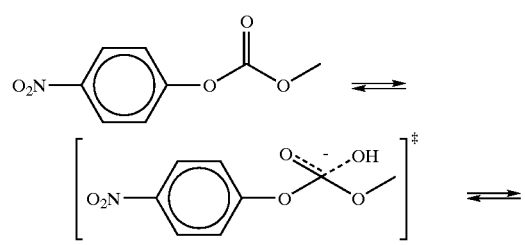

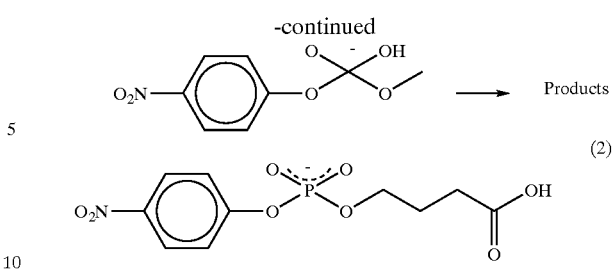

(A) Preparation of the Antigen

4-Nitrophenyl phosphonate (2) was synthesized in five steps from triethyl phosphite and methyl 5-bromopentanoate. Phosphonate (2) was then coupled to the carrier proteins bovine serum albumin (BSA) and keyhole limpet hemocyanin (KLH) in dilute aqueous HCl, pH 5.0, by using 1-(3-(dimethylamino)propyl)-3-ethylcarbodiimide, followed by exhaustive dialysis against aqueous 10 mM phosphate 150 mM NaCl buffer, pH 7.4. Quantitation of the hapten/carrier ratio by hydrolysis of the nitrophenyl phosphonate conjugate typically afforded ratios in the range of 15:1. The orientation and length of the five-carbon spacer was chose to maximize the probability that the antibody would bind the hapten with the phosphonate moiety near the antibody surface and accessible to water.

(B) Preparation of the Monoclonal Antibodies

BALB/C mice were immunized with the BSA-phosphonate conjugate emulsified in complete Freund's adjuvant. A fusion was carried out by standard methods using SP2/0 myeloma as the fusion partner. IgG was purified from ascites fluid by affinity chromatography on protein A coupled Sepharose 4B and dialyzed exhaustively against reaction buffer. Antibodies were judged to be homogeneous by 10% sodium dodecyl sulfate polyacrylamide gel electrophoresis with Coomassie blue staining.

Generation of monoclonal antibodies against the KLH-phosphonate (2) adduct afforded 20 IgG's which were inhibitable in a competition ELISA assay.

The rates of hydrolysis of carbonate I (1) in the presence ($k_{obsd}$) and the absence ($k_{un}$) of 4.4 $\mu$M antibody were determined as a function of substrate concentration. Carbonate hydrolysis was followed in 10 mM Tris-HCl, pH 8.5 at 30° C., by following the increase in absorbance at 400 nm due to nitrophenolate ion release.

The IgG was found to catalyze the hydrolysis of carbonate (1) with kinetics consistent with the Michaelis-Menten rate expression (I) the value of $k_{cat}$ and the Michaelis constant, $K_m$, were found $$v = \frac{k_{cat}[Ig](1)}{K_m + [(1)]} \quad (I)$$

[Ig]+(1)→[Ig(1)]→[Ig]+products to be 1.4±0.2 min and 660+120 $\mu$M, respectively. This IgG had $k_{cat}$=29 min$^{-1}$ and $K_M$=350 $\mu$M, a rate acceleration of 16,000 above background. The IgG was designated catalytic antibody 48G7.

(C) Use of Catalytic Antibody 48G7

The catalytic antibody 48G7 may be used in biosensors as described in Examples 2–7.

EXAMPLE 2

Detecting pH Changes Resulting from the Hydrolysis of p-Nitrophenylcarbonate with a pH-based Catalytic Antibody Biosensor A pH-based catalytic antibody biosensor incorporating catalytic antibodies as enzyme mimics in a configuration similar to that of enzyme electrodes was used to measure the pH change resulting from the catalyzed hydrolysis of methyl p-nitrophenylcarbonate (MpNPC). The catalytic antibody 48G7 has been shown to catalyze the previously described (Scheme I) hydrolysis reaction of MpNPC. The catalytic antibody 48G7 is synthesized and its catalytic activity identified in accordance with the methodology described in Example 1.

Figure 13:
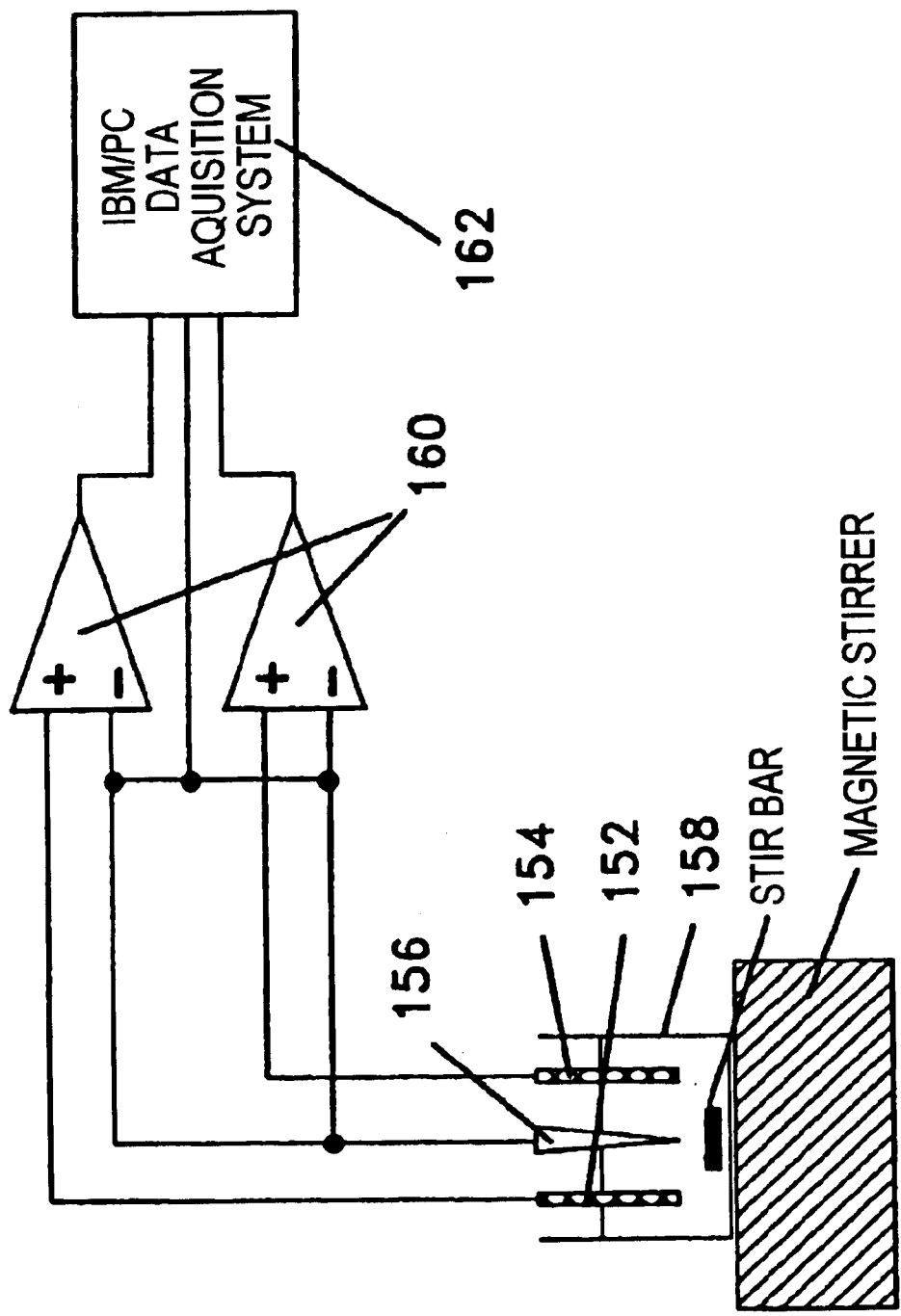
FIG. 13 is a schematic diagram of a pH-based catalytic antibody sensing system.

The catalytic antibody 48G7 produces a relatively small rate of acceleration as compared to natural enzymes. Consequently, the observed pH difference is small but is easily measurable in a reproducible manner. In addition, the spontaneous hydrolysis rate of the substrate MpNPC is significant, causing a background pH change which is not due to the presence of the catalytic antibody. FIG. 13 shows the sensing system that was used to eliminate these limitations. Two miniature pH electrodes 152 and 154 were employed and the difference between the two was monitored. The 48G7 catalytic antibody was trapped on one electrode 152 and nonspecific antibody was trapped on the other electrode 154. A third reference electrode 156 was also used.

The electrical potential of the two miniature pH electrodes 152 and 154 (Microelectrodes Inc., model MI-404) was monitored relative to a single Ag/AgCl reference electrode 156 in an nonthermostated vessel 158 as shown in FIG. 13 using two Keithley 617 electrometers 160. An IBM/PC 162 was used to acquire and store the data from the two electrometers and compute and display the difference between the two signals. The IBM/PC can also be programmed to compute the concentration of the various chemical species based on the acquired and stored data.

The electrodes were configured as previously shown and described in FIG. 1. Referring now to FIGS. 1 and 13, A thin (approximately 0.2 mm) 2.5 mm diameter filter paper (Whatman #2) was placed on the end of each of the flat-glass pH electrodes 152 and 154. A 1 μl aliquot of concentrated (approximately 200 mg/ml) protein was then applied to the filter paper (48G7 catalytic antibody on electrode 152 and pig gamma-G on electrode 154). Next, a thin dialysis membrane (American Scientific Products, Spectra/Por 2) was placed above the filter paper and held in place with a piece of 2.5 mm inner diameter silicone rubber tubing.

The reference electrode 156 and the two pH electrodes 152 and 154 were placed in 2.5 ml of a pH 8.5 buffer (0.14 M KCl, 0.01 M Tris, 0.02% sodium azide) and allowed to stabilize for 36 hours. The difference between the two potentials was stable after only a few minutes in solution. The response to MpNPC was measured after approximately 12 hours in solution (not shown) but the remainder of the measurements were performed after approximately 36 hours in solution.

Figure 14A:
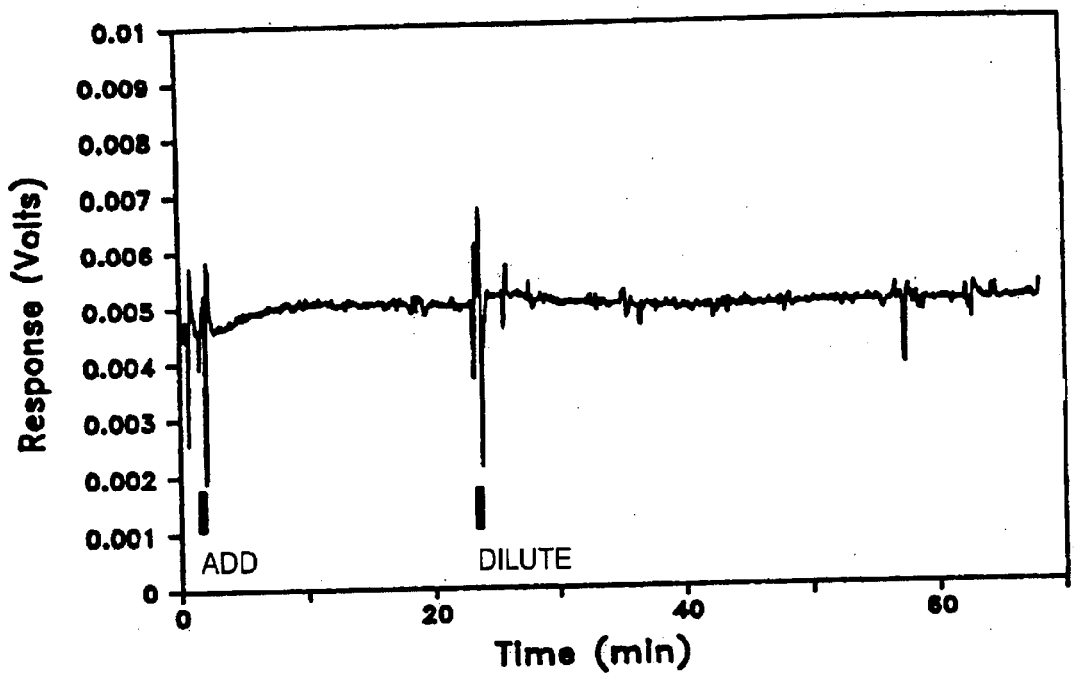
FIG. 14 graphically depicts the differential response of two separate additions and dilutions of methyl p-nitrophenylcarbonate (MpNPC), expressed as a function of time (min) and response (volts) for the biosensor of FIG. 1.
Figure 14B:
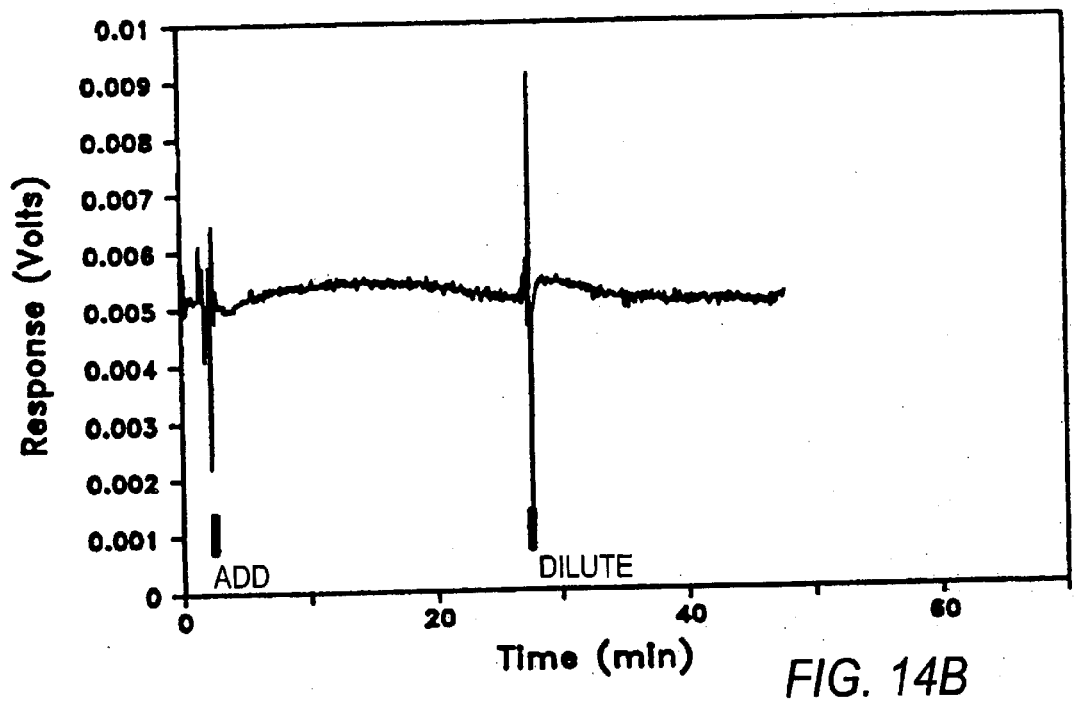

FIG. 14 shows the differential responses of the electrodes to two successive additions and dilutions of MpNPC. At the times shown, 10 μl of 50 mM MpNPC in THF was added ([MPNPC]=220 μM). The solution was then diluted, as indicated, by addition of buffer (final [MpNPC]=31.4 μM).

Figure 15:
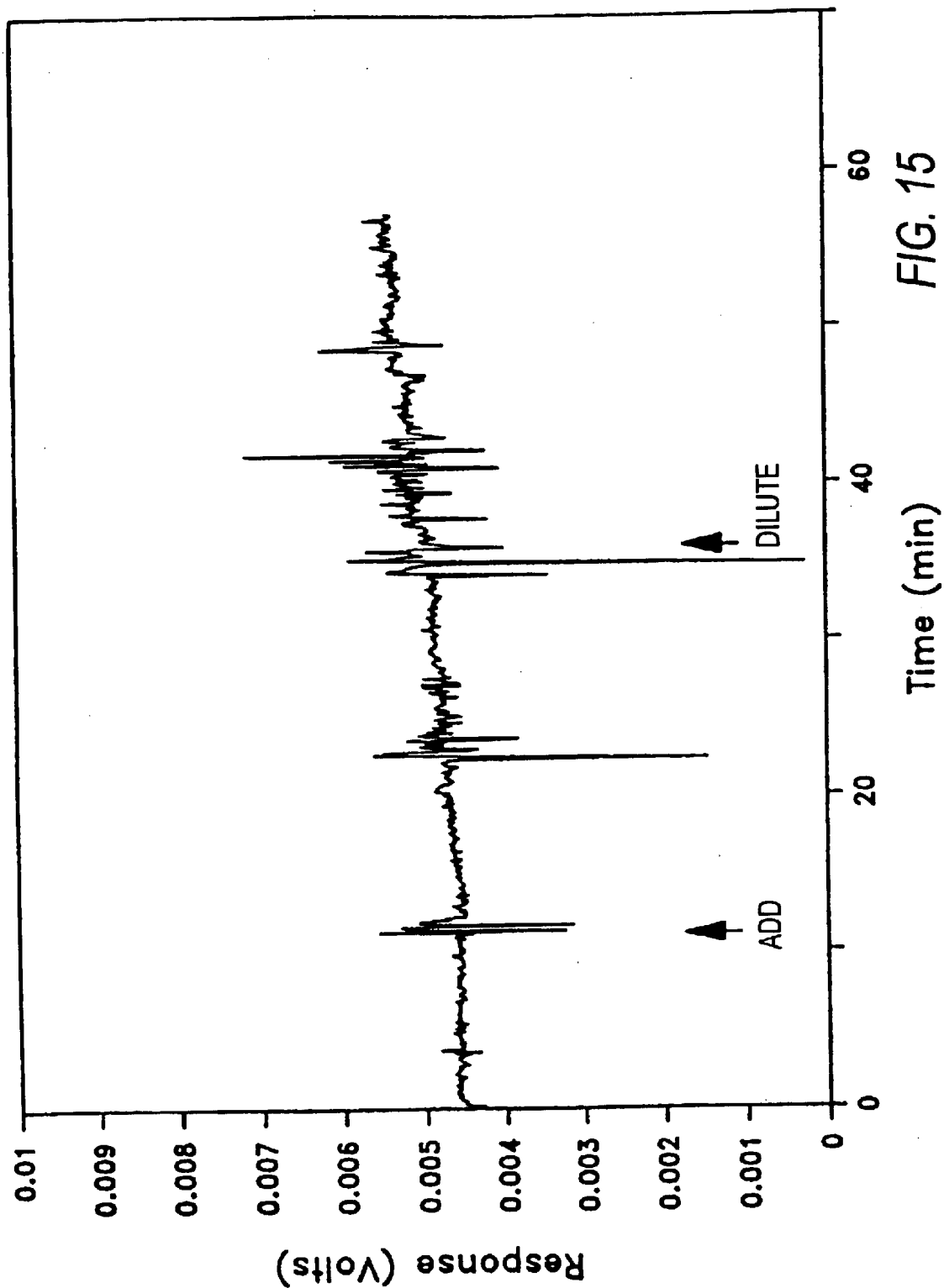
FIG. 15 graphically depicts the differential response of electrodes to addition and dilution of MpNPC in the presence of transition state analog (TSA), methyl p-nitrophenylphosphate as a function of time (min) and response (volts) for the biosensor of FIG. 1.

FIG. 15 shows the response of the electrodes (potential difference) to the addition and dilution of MpNPC after incubating the electrodes in 50 μM transition state analog (TSA) which effectively inhibits the catalysis.

Figure 16:
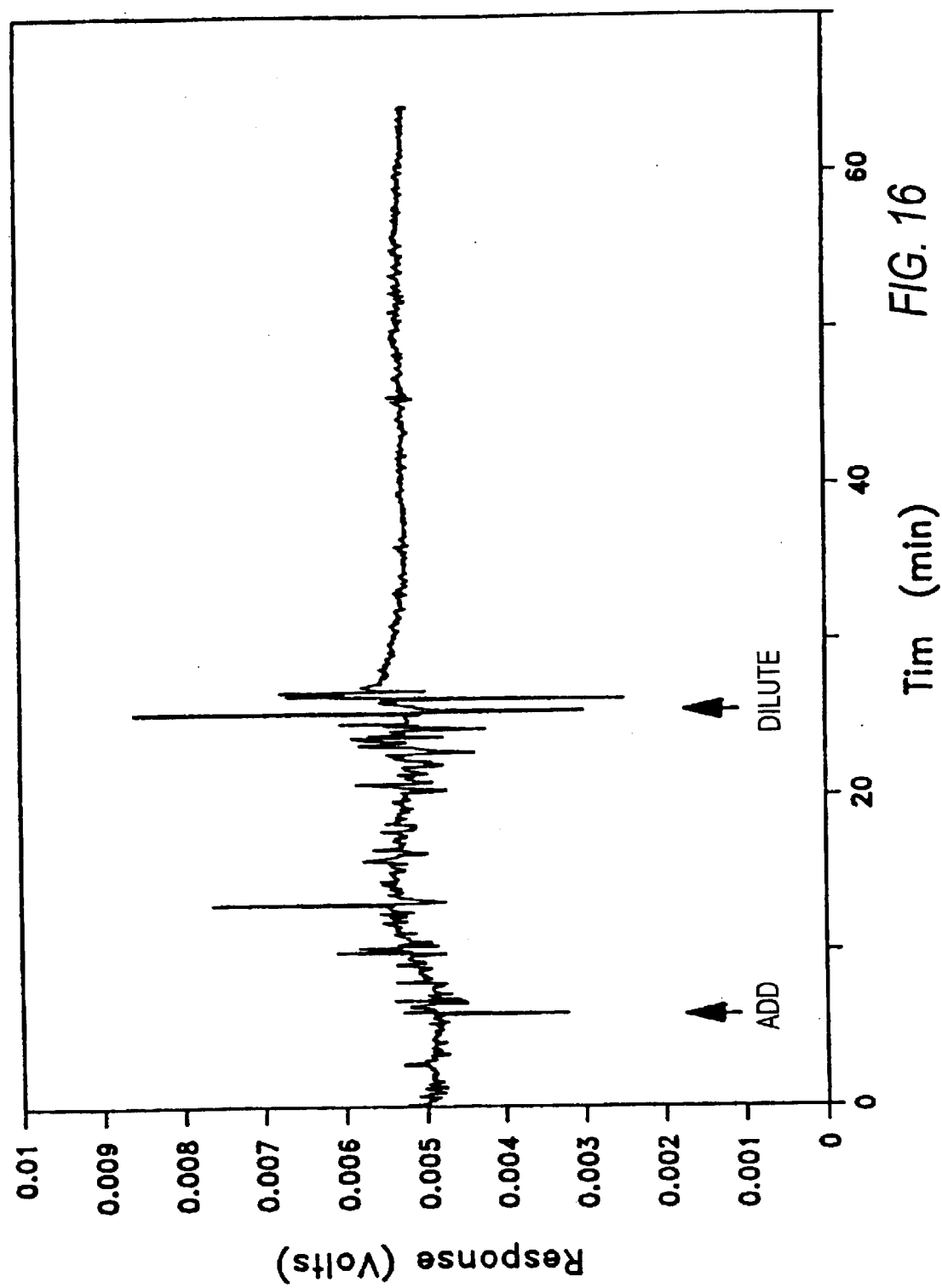
FIG. 16 graphically depicts the differential response of the biosensor of FIG. 1 to addition and dilution of MpNPC after flushing TSA from the biosensor.

FIG. 16 shows the differential response of the electrodes after flushing the TSA from the electrodes by washing for two hours in buffer.

The differential response of the electrodes was small but reproducible. The direction of the response (a positive differential response) was as expected for the production of $H^+$ at the surface of the catalytic antibody electrode. Upon dilution of the sample solution, the response of the sensor system diminished, verifying that the catalytic antibody sensor was reversible. The experimental conditions can undoubtedly be optimized to increase the magnitude of the response.

In the presence of the TSA, the sensor system did not respond to additions of MpNPC as would be expected since the TSA is bound by the catalytic antibody, inactivating its catalytic active site. The lack of any response in the presence of TSA is a positive verification that the response is due to the catalytic activity of the protein on the electrode rather than an experimental artifact. The response of the sensor system was regenerated after exposure to the TSA by soaking the pH sensor in a buffer free of TSA for two hours, verifying once again that the response is reversible and that the lack of response in the presence of TSA was not an artifact. Thus, the loss or inhibition of catalytic activity can be used in this sensor to monitor the concentration of TSA or chemically related species.

EXAMPLE 3

Sensing the Presence of Methyl p-Nitrophenylcarbonate (MpNPC) by Detecting p-Nitrophenoxide (PNP) with an Optical Fiber-Based Catalytic Antibody Biosensor The presence of p-nitrophenoxide (PNP) produced as the result of 48G7 antibody catalyzed hydrolysis of MpNPC, as described and shown in Scheme I above, was detected by using an optical fiber-based catalytic antibody biosensor. FIG. 5 shows a schematic representation of an optical fiber sensor. FIG. 6 depicts the sensing system. Referring to FIGS. 5 and 6, a tungsten lamp is used as the light source 84 with an interference filter 86 between the lamp and excitation fibers 82A to limit the wavelength to the 405 nm region. Filter paper 90 filled with 48G7 catalytic antibody is held on the end of fiber bundle 76 with a thin dialysis membrane 92. The dialysis membrane 92 is secured to the end of the fiber bundle 76 by silicone rubber tubing 94. The catalytic antibody at the end of the optical fiber bundle 76 catalyzes the reaction which forms the chromophore PNP $$(\epsilon_{400} \text{ nm}=18,300 \text{ M}^{-1}\text{cm}^{-1}).$$

The chromophore absorbs a fraction of the light at the end of the fiber bundle, resulting in less reflected light returning to the photomultiplier tube. Because the background spontaneous hydrolysis rate is large, a differential measurement is necessary to determine the response due to the catalytic activity of the antibody. The data were recorded on a Heath strip-chart recorder 96 and later input into a IBM/PC (now shown) for analysis. The IBM/PC can be programmed to compute the concentration of the MpNPC.

The preparation of the optical fiber sensor was nearly identical to that of the pH electrode sensor described above in Example 2. A thin (approximately 0.2 mm) 8 mm diameter filter paper (Whatman #2) was placed on the end of the optical fiber bundle. A 10 μl aliquot of concentrated (approximately 200 mg/ml) 48G7 catalytic antibody was then applied to the filter paper. Next, a thin dialysis membrane (DIACHEMA 10.17) was then placed over the filter paper and held in place with a piece of 6.4 mm inner diameter silicone rubber tubing.

The optical fiber was placed in a light-tight cell 80 containing 5 ml of buffer (identical to buffer used in Example 2) and allowed to stabilize until the transmitted light signal stabilized (about 25 min). Substrate, MpNPC, was added with a GC syringe by momentarily opening the cell and removing the optical fiber. Reference measurements with pig gamma-G protein (noncatalytic protein) replacing the catalytic antibody were made in separate experiments.

The response to MpNPC was measured both in the presence and absence of TSA as well as after regenerating the sensor by washing the TSA from the sensing area with buffer. The results are shown in FIGS. 17 and 18.

Figure 17:
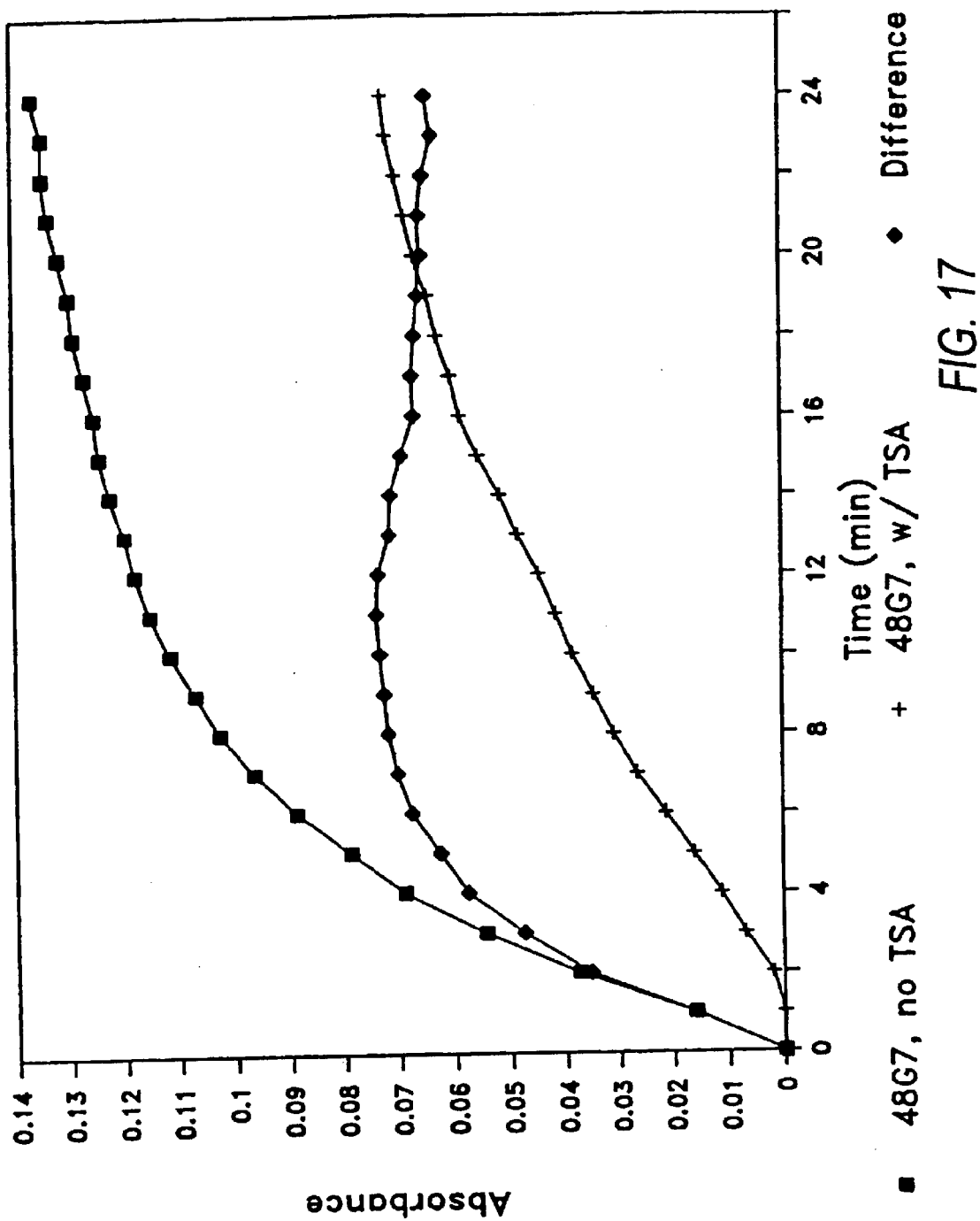
FIG. 17 graphically depicts the response of two separate but identically prepared optical fiber sensors as shown in FIG. 5 to the addition of 250 $\mu$M MpNPC; the square symbols represent the response of the noninhibited 48G7 sensor; the plus symbols are the response of the TSA inhibited sensor; and the diamond symbols represent the differential signal.

FIG. 17 compares the response of two different but identically prepared optical fiber sensors to addition of 250 uM MpNPC; the square symbols represent the response of the noninhibited 48G7 sensor (i.e., in the absence of TSA) and the plus symbols are the response of the TSA inhibited sensor (i.e., in the presence of TSA). The diamond symbols represent the difference between the two signals.

FIG. 18 compares two responses of the same sensor, both in the presence of TSA inhibitor (plus symbols), and after flushing away of TSA inhibitor (square symbols). The diamond symbols represent the differential signal.

The response in the presence of TSA represents the optical absorption due to the spontaneous background hydrolysis of the substrate. In the presence of non-inhibited catalytic antibody a much larger response is observed. The difference represents the response of the sensor due to the presence of catalytic activity of the antibody.

EXAMPLE 4

Detecting the Heat of Reaction from the Hydrolysis of Methyl p-Nitrophenylcarbonate with a Thermistor-Based Calorimetric Catalytic Antibody Biosensor A calorimetric catalytic antibody biosensor incorporating a thermistor, a temperature sensitive transducer, is used to measure the heat of reaction for the hydrolysis of MpNPC using the catalytic antibody 48G7 as a selective catalyst for the reaction as shown in Scheme I above. The biosensor system is shown in FIG. 8. Two columns 120A and 120B (5 mm inner diameter, 25 mm long) packed with protein (48G7 catalytic antibody in 120B and pig gamma-G in 120A) immobilized on controlled pore glass (40–80 mesh, pore diameter 55 nm; Corning Glass Works) are contained in a double wall plexiglass housing 128 which is immersed in a thermostatted water bath (not shown). The protein is immobilized to the controlled pore glass by modification with 3-aminopropyltriethoxysilane and treated with glutaraldehyde according to the procedure of Weetall (33). A two channel peristaltic pump 118 (LKB model 12000) is used to pump a carrier stream of 0.14 M KCl, 0.01 M Tris, 0.02% sodium azide, pH 8.5 solution through the two columns (0.5 ml/min.) 30 kΩ thermistors 122A and 122B (Omega Engineering) are placed at the exit of each of columns 120A and 120B, respectively. A Wheatstone bridge 124 and an electrometer (Keithley model 617) (not shown) are used to monitor the differential resistance. The analog output of the electrometer is monitored using an IBM/PC (not shown) equipped with a data acquisition board (Metrabyte model DAS-16). Samples of MpNPC (10–200 µM) are injected in the carrier stream using a sampling valve 114 with a 100 µl sample loop.

EXAMPLE 5

Detecting Binding of Methyl p-Nitrophenylcarbonate by 48G7 Catalytic Antibody Using Bulk Acoustic Wave Piezoelectric Transducer A bulk acoustic wave piezoelectric transducer incorporating 48G7 catalytic antibody is used to detect the presence of MpNPC by sensing the binding of MpNPC to the antibody. As shown in FIG. 9, AT-cut quartz crystals 131 (1–10 MHz) are coated with thin films (200–800 nm) of aluminum on both sides of the crystals to form aluminum electrodes 129. FIG. 10 shows that the crystals are held with silicone O-rings 135 in plexiglas 137 housing so that only one face is exposed to the solution. 48G7 catalytic antibodies are immobilized on the surface of the aluminum electrodes. Electrical connections to the crystal are made with silver foil 133. A radio frequency amplifier (not shown) is used with the crystal in a feedback loop to drive the crystal at its natural resonant frequency. The frequency of oscillation is measured with a frequency counter (not shown). The measurements are made in a Faraday cage (not shown) to eliminate noise.

The crystal and holder are rigidly held in a 100 ml vessel and 25 ml of 0.14 M KCl, 0.01 M Tris, 0.02% sodium azide, pH 8.5 buffer solution is carefully added by first wetting the face of the crystal with a small amount of the buffer. For measurement of the response to MpNPC, 10–125 µl of 50 mM MpNPC (in THF) are added to the 25 ml of buffer.

Additions of MpNPC are made as described above after the oscillation frequency of the crystals has stabilized. As MpNPC binds to the 48G7 antibody, the natural resonant frequency is perturbed, thereby indicating the presence of the MpNPC. Because this perturbation is thought to represent an equivalent mass change of the crystals themselves, the concentration of MpNPC may be calculated.

EXAMPLE 6

Detecting Binding of Mehtyl p-Nitrophenylcarbonate by 48G7 Catalytic Antibody Using Lipid Bilayer Chemical Sensors FIG. 11 shows a diagram of the catalytic antibody sensor incorporating a planar, supported lipid bilayer membrane as a part of the sensing element. The sensor is fabricated by evaporating a thin film (~500 nm) of silver 140 on a 27×75 mm glass microscope silde through a shadow mask having a 5×5 mm square opening connected to a 0.5×20 mm line (for electrical contact to the square electrode). The top surface 142 of the silver film 140 is chloridized by partially immersing the glass slide (so that the square electrode is immersed but the contact line only partially immersed) in a stirred aqueous solution of 1.0 M KCl and applying a voltage of 0.8 V to the silver electrode versus a silver wire in the same solution with a voltage supply for ten minutes. The glass slide is then washed with distilled water and dried. The hydrogel matrix 138 is applied by spin casting (using a conventional photoresist spinner) a film of 9.5% (w/v) acrylamide, 0.5% (w/v) N,N'-methylene-bis-acrylamide, 0.005% riboflavin-5'-phosphate, and 1% N,N,N',N'- tetramethylethylenediamine in 0.1 M phosphate buffer (pH 7) on the glass slide. The slide is then irradiated with 254 nm ultraviolet light for 60 minutes to induce polymerization of the acrylamide gel. The slide is then stored in 0.1 M KCL solution.

The lipid bilayer membrane 136 (1:1 v/v mixture of phosphatidyl choline and cholesterol) is deposited (from a 0.1% w/v solution in hexane) using the Langmuir-Blodgett technique (34) from a subphase of 0.1 M KCl. The glass is immersed in the subphase before the monolayer is compressed to a surface pressure of 30 mN m$^{-1}$. After compression the slide is withdrawn through the interface at a speed of 3 mm min$^{-1}$ and then reimmersed at the same speed, thus depositing a bilayer of the phospholipid/cholesterol over the polyacrylamide gel. A teflon cylinder (not shown) is then place around the partially immersed slide, creating an enclosed volume around the slide of approximately 50 m. Electrical contact is made to the square electrode and to a Ag/AgCl reference electrode 151 also placed in the enclosed volume of 0.1 M KCl.

The electrical conductivity of the lipid bilayer sensor is monitored by applying a 10 mV, 1 Hz square wave to the cell and measuring the current at the end of each half cycle with a Keithley 617 electrometer interfaced to an IBM/PC.

Catalytic antibodies (48G7) are immobilized to the lipid bilayer membrane by physisorption by adding 100 μl of a concentrated (1 mM in 0.1 M KCl) solution of the antibodies to the 50 ml volume surrounding the lipid bilayer sensor. After allowing 30 minutes for adsorption to occur, the response to MpNPC is measured by adding 20 200 μl of 50 mM substrate in THF and monitoring the conductivity change.

EXAMPLE 7

Detection of Methyl p-Nitrophenylcarbonate (MpNPC) with 48G7 Catalytic Antibodies Using Electrogenerated Chemiluminescence (ECL) and an Optical Waveguide Sensor MpNPC is detected with 48G7 catalytic antibodies using ECL and an optical waveguide sensor. The optical waveguide sensor is shown in FIG. 7 and is prepared by depositing a thin layer of optically transmitting conductive material on the outer surface of the waveguide 100. For example, indium-tin-oxide can be sputtered or very thin films (<10 nm) of gold or platinum can be evaporated through a shadow mask to produce the desired electrode geometry (e.g., 5×5 mm square). Electrical contact to electrode 98 is made with a wire using conductive epoxy and the connection and wire are encapsulated with a suitable non-conductive material such as epoxy or silicone rubber (not shown in FIG. 7).

(A) Preparation of Bifunctional Molecule Containing the Tethered Antigen and TAG The bifunctional molecule which contains N,p-nitrophenylanilide or other related analog as the tethered antigen 108 (which is not bound with a high affinity nor altered chemically by 48G7) and the TAG moiety 106, Ru(bpy)$_3$, is shown below:

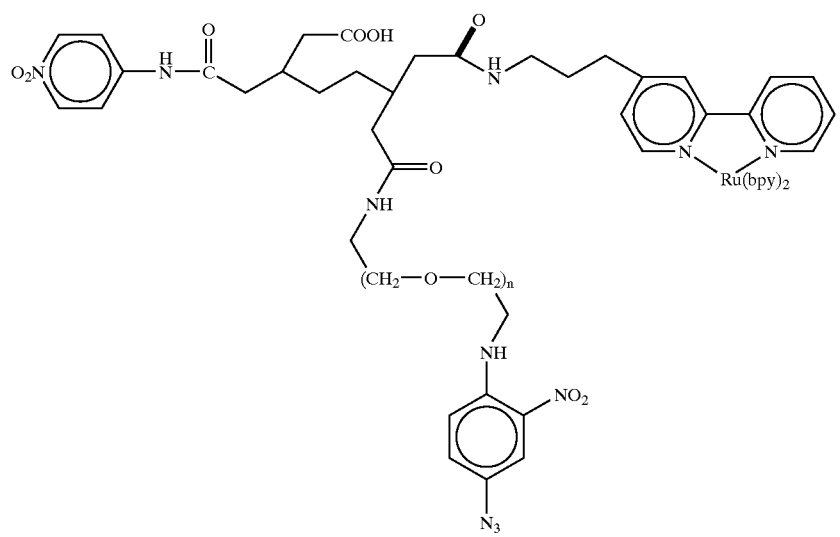

The molecule is synthesized as follows: p-nitroaniline is reacted with EDTA-bis-anhydride to yield 2, as shown.

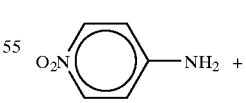

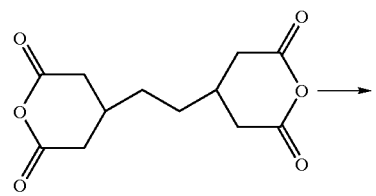

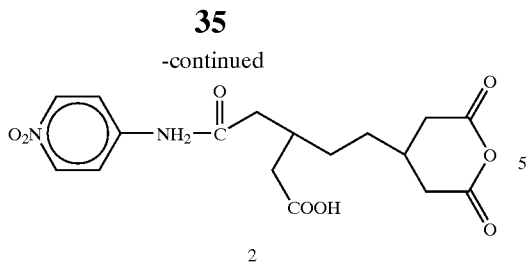

2

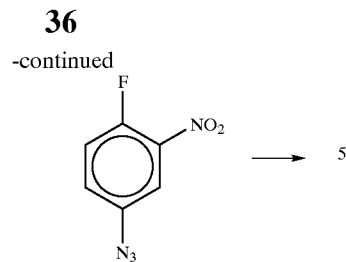

The anhydride group of 2 if coupled to the amine derivatized ruthenium complex, 3, yielding 4.

The bifunctional molecule, 1, is coupled to the catalytic antibody by mixing equal volumes of a 1 mg/ml solution of

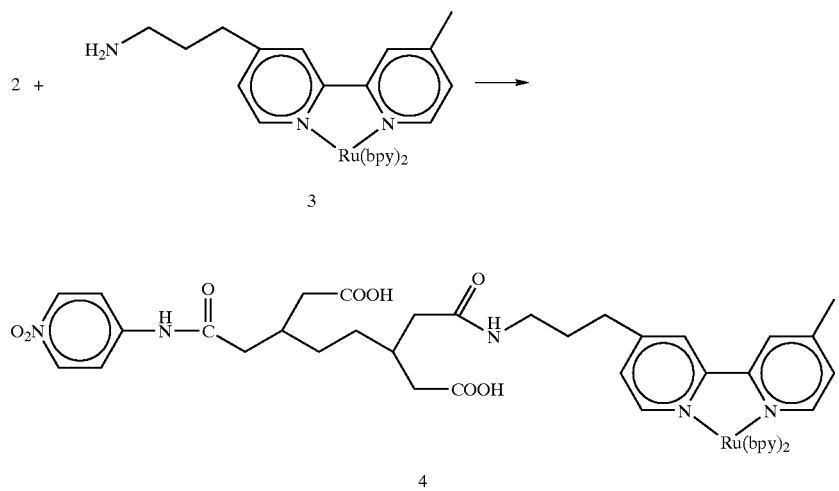

A reactive side group is added to 4 to allow coupling to the antibody by reacting 4 with derivatized poly(ethylene oxide), 5, using dicyclohexylcarbodiimide (DCCI), forming the desired product 1.

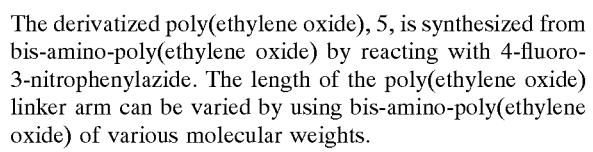

The derivatized poly(ethylene oxide), 5, is synthesized from bis-amino-poly(ethylene oxide) by reacting with 4-fluoro-3-nitrophenylazide. The length of the poly(ethylene oxide) linker arm can be varied by using bis-amino-poly(ethylene oxide) of various molecular weights.

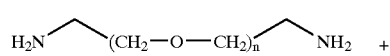

the catalytic antibody in 100 mM KCl and a 10 μM solution of molecule 1. The catalytic antibody binds the tethered antigen, positioning the reactive azide side group of molecule 1 for coupling to the antibody. The azide group can be expected to react with an of several amino acid residues, including lysine, histidine, and tyrosine.

(B) Immobilization of 48G7 Catalytic Antibody

Fab' fragments of the catalytic antibody 48G7 are formed by treating the antibody with pepsin which cleaves off the Fc fragment. Subsequent treatment with alkyl thiol forms the desired Fab' fragments by breaking the interchain disulfide bond. The Fab' fragments with attached bifunctional groups are immobilized to the surface of the electrode by functionalizing the electrode with N-3-maleimidopropyldimethylethoxysilane and then coupling the —SR groups of the catalytic anitibody Fab' fragments to the surface maleimide group.

(C) Detection of MpNPC

The ECL catalytic sensor is calibrated by placing the sensor in a light-tight enclosure in a solution of 50 mM tripropylamine, 0.05% TWEEN 20, and 100 mM KCl and adding MpNPC to give concentrations over the range of 1–500 μM. A platinum auxiliary electrode and a reference electrode (e.g., Ag/AgCl) (not shown) are placed in the solution with the sensor and a potential of +1.5 V versus the reference electrode is applied to the transparent electrode 98 using an electrochemical potentiostat (e.g., EG&G Princeton Applied Research Corp. model 273). The light generated by the ECL reaction is monitored by measuring the output of the photomultiplier tube 112. Measurements of MpNPC in samples of unknown concentration are made by mixing the sample with an equal volume of 100 mM tripropylamine, 0.1% TWEEN 20, and 200 mM KCl and measuring the ECL light generated by the sensor as described in the calibration procedure.

EXAMPLE 8

Detecting Inhibitors Such as Chemical and Biological Warfare Agents with a pH-Based Catalytic Antibody Biosensor A pH-based catalytic antibody biosensor incorporating antibodies which mimic choline ester receptor proteins, such as MOPC167, is used to detect chemical and biological warfare (CBW) agents and other inhibitors. For example, acetylcholine (Ach) is an important neurotransmitter which is stored in vesicles in the synaptic terminals of cholinergic neurons and is released by neural impulses. The released neurotransmitter diffuses across the synaptic cleft and binds to Ach receptors in the post-synaptic neural membranes where the binding event stimulates a neural impulse. Many CBW agents act by binding to the Ach receptors and blocking the transmittance of neural impulses across the neural synapse. The catalytic antibody MOPC167 binds choline esters (mimicking the neural Ach receptors) and catalyzes their hydrolysis. As a specific example, MOPC167 catalyzes the hydrolysis of p-nitrophenyl N-trimethyl ammonioethyl carbonate (NTAC) according to the reaction shown in Scheme III above. The hydrolysis of choline esters, catalyzed by MOPC167, produces hydrogen ions which can be detected using a pH-based biosensor as described in Example 2. Thus, Ach inhibitors are detected by sensing the change in hydrogen ion concentration resulting from catalysis inhibition.

In this example, MOPC167 is trapped on the end of a minature pH electrode and a nonspecific IgA antibody is entrapped on a second (control) pH electrode. A third reference electrode is also used. This configuration is identical to that of Example 2 as shown in FIG. 13. Two electrometers are used to measure the potential of each pH electrode relative to the Ag/AgCl reference electrode. The data are acquired using a microcomputer (IBM/PC) which calculates and displays the difference between the response of the two pH electrodes.

The electrodes are configured identically to that of Example 2 as shown in FIG. 1. A thin (approximately 0.2 mm) 2.5 mm diameter filter paper (Whatman #2) is placed on the end of the flat-membrane pH electrode (Microelectrodes Inc., model MI-404). A 1 l aliquot of concentrated protein (approximately 200 mg/ml); MOPC167 catalytic antibody on one electrode and immunoglobulin A on the second) is then applied to the filter paper. A thin dialysis membrane (American Scientific Products, Spectra/Por 2) is then placed over the filter paper and held in place with a piece of 2.5 mm inner diameter silicone rubber tubing.

The reference electrode and two pH electrodes are placed in 2.5 ml of a pH 8.5 buffer (0.14 M KCl, 0.01 M Tris, 0.02% sodium azide) and allowed to stabilize until stable potentials are attained. The response of the system to NTAC is measured multiple times by adding 0.025 ml of 10 mM NTAC chloride in buffer ([NTAC]=0.1 mM). The differential response is monitored on a microcomputer.

Attenuation of the response to NTAC by addition of inhibitor is measured by placing the electrodes in 2.5 ml of buffer solution containing the inhibitor for 30 minutes. 0.025 ml of 10 mM NTAC chloride in buffer is then added and the response compared to the response in the absence of the inhibitor.

In this manner, a calibration curve is constructed which relates the inhibitor concentration to the magnitude of the response to NTAC. An effective inhibitor blocks the binding of NTAC to the MOPC167 catalytic antibody and hydrolysis does not occur; consequently, the differential pH response is zero. In this manner the MOPC167 can be used in conjunction with a pH-based sensor system to mimic choline ester receptors and to determine the presence of CBW agents and other inhibitors of choline ester receptors.

REFERENCES

1. M. Cremer, *Z. Biol.* 47, 562 (1906).
2. F. Haber and Z. Klemensiewicz, *Z. Phys. Chem.,* 67, 385 (1909).
3. I. Karube, *Biotechnology and Genetic Engineering Reviews,* 2, 313 (1984).
4. H. Y. Neujahr, "Biosensors for Environmental Control," *Biotechnol. Genet. Eng. Rev.,* 1, 167–186 (1984).
5. F. W. Scheller, F. Schubert, R. Renneberg, H. G. Muller, M. Janchen, and H. Wiese, *Biosensors,* 1, 1 (1985).
6. G. G. Guilbault, "Medical and Biological Applications of Electrochemical Devices," Ch. 9 (Edited by J. Koryta), John Wiley: Chichester (1980).
7. a) M. Y. Keating and G. A. Rechnitz, "Potentiometric Digoxin Antibody Measurements with Antigen-Ionophore Based Membrane Electrodes," *Anal. Chem.,* 56, 801–806 (1984).
7. b) H. Freiser, editor, "Ion-Selective Electrodes in Analytical Chemistry," Vols. 1 and 2, Plenum Press: New York (1980).
8. J. Savory, R. L. Bertholf, J. C. Boyd, D. E. Bruns, R. A. Felder, M. Lovell, J. R. Shipe, M. R. Wills, J. D. Czaban, K. F. Coffey, and K. M. O'Connell, "Advances in Clinical Chemistry Over the Past 25 Years," *Anal. Chim. Acta,* 1980, 99 (1986).
9. M. Aizawa, A. Morioka, and S. Suzuki. *J. Membrane Sci.,* 4, 221 (1978).
10. G. Blackburn, "Molecular Adsorption Measurement with Chemically Sensitive Field Effect Transistors," Ph.D. Dissertation, University of Utah (1983).
11. G. F. Blackburn, "Chemically Sensitive Field Effect Transistors" in "Biosensors: Fundamentals and Applications," (A. P. F. Turner et al., eds.), 481–530, Oxford University Press, Oxford England (1987).
12. J. Janata and G. F. Blackburn, "Immunochemical Potentiometric Sensors," *Annals of the New York Academy of Sciences,* 428, 286 (1984).
13. a) "Bioanalytical Applications of Fiber-Optic Chemical Sensors," *Anal. Chem.,* 58 766A (1986); b) J. I. Peterson and G. G. Vurek, "Fiber-Optic Sensors for Biomedical Applications," *Science,* 224, 123 (1984).
14. A. M. Smith, "Waveguide Immunoassays," *Analytical Proceedings,* 24, 15–17 (1987).
15. J. I. Peterson, S. R. Goldstein and R. V. Fitzgerald, *Anal. Chem.,* 52, 864 (1980).
16. J. I. Peterson, R. V. Fitzgerald, and D. K. Buckhold, *Anal. Chem.,* 56, 62 (1984).
17. G. G. Vurek, P. J. Feustel, and J. W. Severinghouse, "A Fiber Optic $pCO_2$ Sensor," *Ann. Biomed. Eng.,* 11, 499 (1983).
18. J. S. Schultz, S. Mansouri, and I. J. Goldstein, *Diabetes Care,* 5, 245 (1982).
19. K. I. Lundstrom, H. R. Arwin, E. Ricke, G. Sielaff, and N. Hennrich, "Immunoassay Without Labels," European patent 73980-A (1983).
20. B. Liedberg, C. Nylander, and I. Lundstrom, "Surface Plasmon Resonance for Gas Detection and Biosensing," *Sensors and Actuators,* 4, 299 (1983).

21. B. Danielsson et al., "Enzyme Thermistor Devices and Their Analytical Applications", *App. Biochem. and Bioengin.,* 3, 97–143 (1981).
22. B. Danielsson, and K. Mosbach, "Theory and Application of Calorimetric Sensors," in "Biosensors: Fundamentals and Applications," (A. P. F. Turner, K. Karube, and G. S. Wilson, eds.), p. 575–595. Oxford University Press, Oxford, England, 1987.
23. a) G. Sauerbrey, *Z. Phys.,* 155, 206 (1959); b) G. Sauerbrey, *Z. Phys.,* 178, 457 (1964).
24. J. F. Alder and J. J. McCallum, "Piezoelectric Crystals for Mass and Chemical Measurements," *The Analyst,* 108, 1169 (1983).
25. J. E. Roederder and G. J. Bastiaans, *Anal. Chem.,* 55, 2333 (1983).
26. M. Thompson, C. L. Arthur, and G. K. Dhaliwal, "Liquid Phase Piezoelectric and Acoustic Transmission Studies of Interfacial Immunochemistry," *Anal. Chem.,* 58, 1206 (1986).
27. J. Janata, R. J. Huber, and M. Thompson, "Electrochemical Sensor for Selective Detection of Chemical Species— Esp. for Gas or Liquid Use in Detecting Enzyme, Antibody, Antigen etc. With Accuracy," European Patent No. 851023.
28. H. M. McConnell, "Lipid Membrane Electroanalytical Elements and Method of Analysis Therewith," U.S. Pat. No. 4,490,216.
29. S. A. Barker, "Immobilization of the Biological Component of Biosensors," in "Biosensors: Fundamentals and Applications," (A. P. F. Turner, I. Karube, and G. S. Wilson, eds.), p. 85–99, Oxford University Press, Oxford, England, 1987.
30. (a) A. Arya, U. J. Krull, M. Thompson, and H. E. Wong, "Langmuir-Blodgett Deposition of Lipid Films on Hydrogel as a Basis for Biosensor Development," *Anal. Chim. Acta,* 173, 331 (1985); (b) U. J. Krull, M. Thompson, E. T. Vandenberg, and H. E. Wong, "Langmuir-Blodgett Film Characteristics and Phospholipid Membrane Ion Conduction. Part 1. Modification by Chloresterol and Oxidized Derivatives," *Anal. Chim. Acta,* 174, 83 (1985); (c) U. J. Krull, M. Thompson, E. T. Vandenberg, and H. E. Wong, "Langmuir-Blodgett Film Characteristics and Phospholipid Membrane Ion Conduction. Part 2. Ethylenic Acyl Chain Oxidation," *Anal. Chim. Acta,* 174, 95 (1985).
31. J. W. Pollack and P. G. Schultz, *Science,* 234, 1570–1573 (1986).
32. M. Potter and M. Leon, "Three IgA Myeloma Immunoglobulins from BALB/C Mouse: Precipitation with Pneumococcal Polysaccharide," *Sci.,* 162, 369 (1968).
33. H. H. Weetal, *Methods in Enzymology,* (K. Mosbach, ed.), 44, 134–148, Academic Press, New York (1976).
34. G. L. Gaines, "Insoluble Monolayers at Liquid-Gas Interfaces," Intersciences Publishers:New York (1965).

We claim:

1. A method for detecting an analyte of interest in an environment wherein the analyte is consumed or generated during the course of a chemical reaction, which method comprises:

(a) contacting said analyte of interest to bind to a catalytic monoclonal antibody or fragment thereof immobilized on a surface of, or on a surface associated with, a sensing means, said catalytic monoclonal antibody or fragment thereof being capable of catalyzing a chemical reaction whereby said chemical reaction occurs in said environment, wherein at least one reactant is converted to at least one product and thereby forming an antibody-reactant complex, catalytically converting said complexed reactant to said product and releasing said product from said complex, thereby regenerating said antibody or fragment;

(b) detecting by the sensing means the binding of the analyte of the catalytic monoclonal antibody and transducing information related to said binding by a transducer;

(c) processing the information generated by the transducer; and (d) releasing the analyte from the antibody by catalyzing a reaction of said analyte and thereby detecting the analyte of interest in the environment.

2. The method of claim 1, which further comprises releasing the analyte from the catalytic monoclonal antibody or fragment in the same environment in which the binding of the analyte to the antibody or fragment took place.

3. The method of claim 1, which further comprises releasing the analyte from the catalytic monoclonal antibody or fragment by removing the analyte-antibody complex to a second environment, said environment being conducive to a chemical reaction which the catalytic monoclonal antibody or fragment thereof catalyzes.

* * * * *